United States Patent [19]

Dykstra et al.

[11] E Re. 30,811

[45] Reissued Dec. 1, 1981

[54] SUBSTITUTED PIPERIDINES THERAPEUTIC PROCESS AND COMPOSITIONS

[75] Inventors: Stanley J. Dykstra; Joseph L. Minielli, both of Evansville, Ind.

[73] Assignee: Mead Johnson & Company, Evansville, Ind.

[21] Appl. No.: 98,008

[22] Filed: Nov. 28, 1979

Related U.S. Patent Documents

Reissue of:

[64] Patent No.: 4,064,254
Issued: Dec. 20, 1977
Appl. No.: 734,583
Filed: Oct. 21, 1976

U.S. Applications:

[60] Division of Ser. No. 620,907, Oct. 8, 1975, Pat. No. 4,000,143, which is a division of Ser. No. 384,341, Jul. 31, 1973, Pat. No. 3,931,195, which is a continuation-in-part of Ser. No. 120,754, Mar. 3, 1971, abandoned.

[51] Int. Cl.[3] ..... A61K 31/445; A61K 31/455

[52] U.S. Cl. ..... 424/266; 424/267

[58] Field of Search ..... 424/266, 267

[56] References Cited

U.S. PATENT DOCUMENTS

| | | | |
|---|---|---|---|
| 2,686,784 | 8/1954 | Finkestein et al. | 260/293 |
| 2,780,577 | 2/1957 | Phillips et al. | 424/267 |
| 3,192,213 | 1/1965 | Krapcho | 260/253 |
| 3,789,072 | 1/1974 | Bernstein | 260/557 D |
| 3,931,195 | 1/1976 | Dykstra et al. | 260/293.58 |

OTHER PUBLICATIONS

Lawson, J. Pharm. Exp. Therap., 160, pp. 21–31 (1968).
Krapcho et al., J. Med. Chem., 6, p. 219 (1963).
Krapcho et al., J. Med. Chem., 7, pp. 376–377 (1964).
Krapcho et al., J. Med. Chem., 9, pp. 809–812 (1966).
Krapcho et al., J. Med. Chem., 12, pp. 164–166 (1969).
Phillips, J. Am. Chem. Soc., 72, pp. 1850–1852 (1950).

*Primary Examiner*—Stanley J. Friedman
*Attorney, Agent, or Firm*—Robert H. Uloth; Robert E. Carnahan

[57] ABSTRACT

The compounds are of the heterocyclic class of 2-phenethylpiperidines having an amido substituent in the ortho position of the phenethyl moiety. Substituents in the ortho position include formamido, benzamido, cinnamamido, 2-thiophenecarboxamido, alkanesulfonamido and alkanoylamido. They are useful as antiarrhythmic and/or antiserotonin agents. The novel compounds are prepared by reaction of appropriately substituted o-aminophenethylpiperidines and the carbonyl or sulfonyl halides or anhydrides. Typical embodiments of this invention are 4-methoxy-2′-[2-(1-methyl-2-piperidyl)ethyl]benzanilide and 2′-[2-(1-methyl-2-piperidyl)ethyl]cinnamanilide.

22 Claims, No Drawings

SUBSTITUTED PIPERIDINES THERAPEUTIC PROCESS AND COMPOSITIONS

Matter enclosed in heavy brackets [ ] appears in the original patent but forms no part of this reissue specification; matter printed in italics indicates the additions made by reissue.

CROSS-REFERENCE TO RELATED APPLICATIONS

This application is a division of co-pending U.S. application Ser. No. 620,907 filed Oct. 8, 1975 and now U.S. Pat. No. 4,000,143 granted Dec. 28, 1976, which is a division of then co-pending U.S. application Ser. No. 384,341 filed July 31, 1973 and now U.S. Pat. No. 3,931,195 granted Jan. 6, 1976, which is a continuation-in-part of then co-pending U.S. application Ser. No. 120,754 filed Mar. 3, 1971, now abandoned.

BACKGROUND OF THE INVENTION

The present invention is concerned with certain heterocyclic organic compounds which can be referred to as substituted piperidines and acid addition salts thereof. In particular, this invention relates to physiologically active novel piperidine compounds which are particularly effective as antiarrhythmic and antiserotonin agents. It is also concerned with chemical intermediates useful in the preparation of the piperidine compounds. Other features of the invention are pharmaceutical compositions containing the piperidines as active ingredients and a therapeutic process for producing antiserotonin and antiarrhythmic effects in mammals by administration of them.

Agents which antagonize serotonin are of interest in experimental biology and in treatment of various physiological disorders such as migraine headache, serotonin producing tumors, toxemia in pregnancy, habitual abortion and management of various inflammatory and allergic reactions. Methysergide and lysergide are well known antiserotonin agents. Other serotonin antagonists which have been reported in the prior art literature on the subject are 2'-(3-dimethylaminopropylthio)cinnamanilide and related compounds disclosed by Krapcho, et al., J. Med. Chem., 6, 219 (1963); 7, 376 (1964); 9,809, (1966); and 12, 164 (1969); and U.S. Patent 3,192,213.

A number of structurally unrelated chemical substances have been employed in the treatment of cardiac arrhythmia; refer to A. Burger, Medicinal Chemistry, 3rd Edition, pages 1082–1085 (Wiley). One of the most important drugs in clinical treatment of disorders of cardiac rhythm is quinidine. Another chemical agent which has been used as an antiarrhythmic is the local anesthetic procaine amide. Still other antiarrhythmic agents are lidocaine, and diphenylhydantoin. None of these compounds are structurally related to the piperidines of the present invention.

SUMMARY OF THE INVENTION

This invention relates to a series of substituted piperidines characterized by Formula I and Formula XII and non-toxic pharmaceutically acceptable acid addition salts thereof.

Formula I

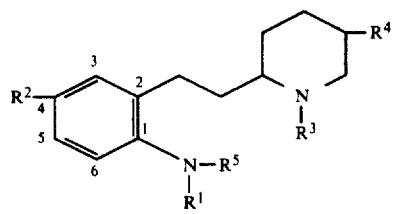

Formula XII

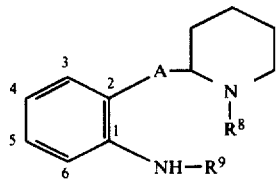

The substances of Formula I and Formula XII are new compositions of matter possessing valuable pharmacological properties which render them useful as synthetic medicinals. In particular, the substituted piperidines of Formula I and Formula XII exhibit utility as antiserotonin and/or antiarrhythmic agents in standard pharmacological tests in mammals. This invention also is concerned with the production of the compounds of Formulas I and XII from novel chemical intermediates, pharmaceutical compositions containing them and a therapeutic process for producing an antiserotonin effect in mammals comprising the administration of such compounds thereto. Another feature of this invention is a therapeutic process for producing an antiarrhythmic effect in mammals by administration of compounds of Formula I wherein $R^5$ is $R^6$ substituted cinnamoyl as depicted by Formula Ia or $R^7$ substituted benzoyl as depicted by Formula Ib.

Still another feature of this invention provides novel o-aminophenethylpiperidines of Formula II which are useful as chemical intermediates in the production of compounds of Formula I.

Formula II

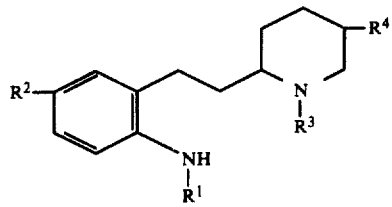

In the compounds characterized by the above general Formulas I and II, the $R^1$ substituent stands for hydrogen or lower alkyl. The substituent $R^2$ represents hydrogen, lower alkoxy or methylenedioxy attached in the benzenoid 4,5-position. $R^3$ stands for hydrogen or a lower alkyl substituent. Substituent $R^4$ represents hydrogen, lower alkyl, or a dialkylcarboxamido substituent wherein the dialkyl groups are lower alkyl.

Substituent $R^5$ represents radicals selected from the group comprised of lower alkanoyl of from 1 to 4 carbon atoms inclusive, lower alkanesulfonyl of from 1 to 4 carbon atoms inclusive,

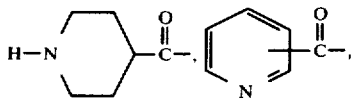

"isonipecotoyl" "pyridylcarbonyl"

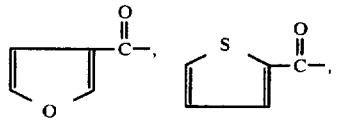

"3-furylcarbonyl" "2-thiophenecarbonyl"

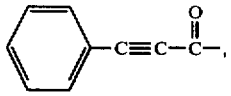

"phenylpropioloyl"

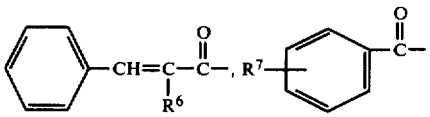

"cinnamoyl" "benzoyl"

The symbol $R^6$ represents hydrogen or lower alkyl and $R^7$ is selected from the group consisting of hydrogen, halogen, trifluoromethyl, amino, dimethylamino, hydroxy, acetoxy, carboxy, alkylthio of from 1 to 4 carbon atoms inclusive, alkyl of from 1 to 4 carbon atoms inclusive, lower alkoxy of from 1 to 4 carbon atoms inclusive, and wherein when $R^7$ is hydrogen or alkoxy the phenyl ring can have up to 2 additional alkoxy substituents of from 1 to 4 carbon atoms inclusive.

In the compounds characterized by Formula XII, the symbol $R^8$ represents hydrogen or lower alkyl. The symbol $R^9$ represents a radical selected from the group consisting of cinnamoyl or

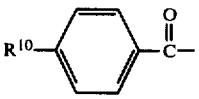

wherein $R^{10}$ is lower alkoxy. The symbol "A" represents a divalent radical selected from the group consisting of $$-CH_2-,\ -\underset{\underset{CH_3}{|}}{CH}-,\ -\underset{\underset{OH}{|}}{CH}-,\ -\underset{\underset{CH_3}{|}}{CHCH_2}-,\ -\underset{\underset{CH_3}{|}}{CH_2CH}-,\ -\underset{\underset{OH}{|}}{CHCH_2CH_2}-,\ \text{and}\ -(CH_2)_3-.$$

It is to be understood that the term "lower alkyl" and "lower alkoxy" as used herein refers to carbon chains which include both straight and branched chain carbon radicals of from 1 to 4 carbon atoms inclusive. Illustrative of these radicals are carbon chains which can be methyl, ethyl, propyl, isopropyl, 1-butyl, 1-methylpropyl, 2-methylpropyl and tert.-butyl.

Compounds which are particularly preferred for their strong antiserotonin activity are compounds of Formula Ia.

Formula Ia

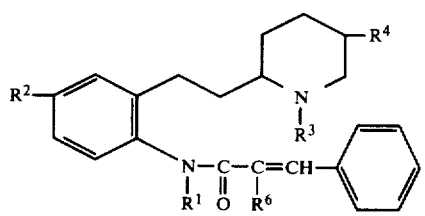

wherein $R^1$, $R^2$, $R^3$, $R^4$ and $R^6$ have the meanings hereinabove given for Formula I. Representative of these compounds is the individually preferred compound 2'-[2-(1-methyl-2-piperidyl)ethyl]cinnamanilide.

Compounds of the present invention which are particularly preferred for their strong antiarrhythmic activity are those of Formula Ib.

Formula Ib

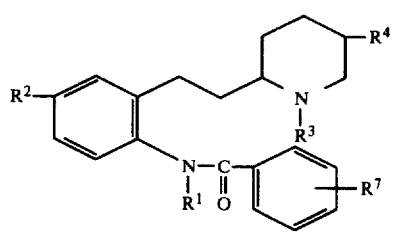

wherein $R^1$, $R^2$, $R^3$, $R^4$, and $R^7$ have the meanings hereinabove given for Formula I. Representative of these compounds are the individually preferred compounds 4-methoxy-2'-[2-(1-methyl-2-piperidyl)ethyl]benzanilide, and 2'-[2-(1-methyl-2-piperidyl)ethyl]-3,4,5-trimethoxybenzanilide.

A still further group of preferred compounds are those characterized by Formula Ib wherein $R^1$, $R^2$, and $R^4$ are hydrogen, $R^3$ is methyl and $R^7$ is hydrogen or alkoxy.

A particularly preferred antiarrhythmic compound of Formula XII is 2'-[3-(1-methyl-2-piperidyl)propyl]-p-anisanilide.

The o-aminophenethylpiperidines of Formula II are considered to be another aspect of the present invention. They are particularly useful as chemical intermediates in the preparation of compounds of Formula I. Apart from being particularly suitable as key intermediates in the preparation of compounds of Formula I, some of the members such as 2-(o-aminophenethyl)-1-methylpiperidine have antiarrhythmic properties.

A compound of Formula XII particularly preferred as an antiarrhytmic agent is 2-[2-[(p-methoxybenzyl-)amino]phenethyl]-1-methylpiperidine and non-toxic pharmaceutically acceptable salts thereof.

It will be apparent to those skilled in the art that the compounds of Formula I, Formula II and formula XII exists in at least one racemic stereoisomeric form since they contain one asymmetric carbon atom (the 2 position of the piperidine ring). Whenever the $R^4$ substituent is not hydrogen, an additional asymmetric carbon atom (the 5 position of the piperidine ring) is present and two racemic modifications exist. Such mixture of racemates can be separated into the individual racemic compounds on the basis of physico-chemical differences such as solubility; for example, by fractional crystallization of the basis or as acid addition salts thereof or by chromatography. Optically active stereoisomers are obtained by resolution methods well known to the art such as the use of optically active acids.

It is to be understood that as used herein, the term "non-toxic pharmaceutically acceptable acid addition salts" refers to a combination of compounds of the present invention with relatively non-toxic inorganic or organic acids. Illustrative of suitable acids which may be used are sulfuric, phosphoric, hydrochloric, hydrobromic, hydroiodic, sulfamic, methanesulfonic, benzenesulfonic, para-toluenesulfonic, acetic, lactic, succinic, maleic, mucic, tartaric, citric, gluconic, benzoic, cinnamic, isethionic and related acids.

The compounds characterized by Formula I and Formula XII exhibit valuable antiarrhythmic activity in mammals. These antiarrhytmic effects are illustratively demonstrated in standard in vitro and in vivo pharmacological tests.

In the dog, for example, electrically or aconitine induced arrhythmia is prevented by oral or parenteral administration of the piperidines of Formula I according to the following in vivo test.

The chest of an anesthetized dog is opened in the midline and the right and left atrial appendages exposed through small slits in the pericardium. Bypolar recording electrodes are affixed to the atrial surfaces and a 4×4 mm. piece of clean cloth is fixed to the surface of the right auricular appendage. Control recordings are made of various heart functions including femoral arterial blood pressure and right and left atrial electrograms. Atrial arrhythmia is then induced by placing 3–5 drops of a solution of aconitine on the cloth which is fixed to the right atrium. An irregular, rapid atrial rate is produced within one minute. Throughout the experiment, fresh aconitine is (2–3 drops) placed on the cloth at 10 minute intervals. The test compound is administered intravenously five minutes after the initial establishment of the arrhythmia and infusion continued at a slow rate until an effective does which re-establishes normal rhythm of the heart is obtained.

Intravenous administration of as little as 0.8 mg./kg. of 4-methoxy-2'-[2-(1-methyl-2-piperidyl)ethyl]benzanilide, a preferred compound of the present invention, effectively restores normal cardiac rhythm to aconitine induced arrhythmia in the dog. A well known antiarrhythmia agent such as quinidine administered in the same manner has an effective dose of 6.0 mg./kg. When arrhythmia is induced electrically, the effective dose of 4-methoxy-2'-[2-(1methyl-2-piperidyl)-ethyl]benzanilide is 1.9 mg./kg. Under like conditions, the effective dose for quinidine is 14 mg./kg.

Intraduodenal administration, which is a measure of oral effectiveness, of 4-methoxy-2'-[2-(1-methyl-2-piperidyl)ethyl]benzanalide prevents aconitine induced arrhythmia in the dog at a dose of less than 10 mg./kg. while the effective dose in the prevention of aconitine induced arrhythmia of quinidine is greater than 14 mg./kg.

Another in vivo test involves the inhibition of chloroform induced arrhythmia in the mouse according to the method of J. W. Lawson, J. Pharmacol. Exp. Therap., 160, 22 (1968). Intraperitoneal administration of 4-methoxy-2'-[2-(1-methyl-2-piperidyl)ethyl]benzanilide to the mouse prevents chloroform induced arrhythmia at an $ED_{50}$ of 7.1 mg./kg. compared to an $Ed_{50}$ of 83 for quinidine.

An in vitro test which demonstrates the antiarrhythmic effects of the compounds of the present invention employs the rabbit atrium. In this test, the left atrium is placed in Chenoweth's solution warmed to 30° C. and irrigated with 95% oxygen: 5% carbon dioxide. The lower end of the atrium is attached to a small hook fixed in the bath and the upper end is connected to a transducer to record contractile activity. The atrium is electrically stimulated at a basic rate of 30 per minute employing square wave pulses of 10 millisecond duraction at 1.2–1.5×threshold voltage. A test compound is introduced into the bath and the test repeated after a 5 minute interval. A dose-response relationship is obtained by additional doses of the test compound. The potency of a test agent can be expressed as the effective concentration which produces 50% of the maximal increase in the measured refractory period of the steady state atrium. This value is designated the $EC_{50}$.

In the in vitro rabbit atrium test, the $EC_{50}$ of 4-methoxy-2'-[2-(1-methyl-2-piperidyl)ethyl]benzanilide is 2.4 microgram per milliliter while the value for quinidine is 18.0 microgram per milliliter.

Examplary of compounds of the present invention which have particularly good antiarrhythmic properties are:

2'-[2-(1-methyl-2-piperidyl)ethyl]benzanilide,
4-hydroxy-2'-[2-(1-methyl-2-piperidyl)ethyl]benzanilide,
4-chloro-2'-[2-(1-methyl-2-piperidyl)ethyl]benzanilide,
4-amino-2'-[2-(1-methyl-2-piperidyl)ethyl]benzanilide,
4-acetoxy-2'-[2-[2-(1-methyl-2-piperidyl)ethyl]benzanilide,
2'-[2-(1-methyl-2-piperidyl)ethyl]-3,4,5-trimethoxybenzanilide,
2'-[2-(1-methyl-2-piperidyl)ethyl]-2-thiophenecarboxanilide,
2'-[2-(1-methyl-2-piperidyl)ethyl]methanesulfonanilide,
2'-[2-(1-methyl-2-piperidyl)ethyl]acetanilide,
2'-[2-(1-methyl-2-piperidyl)ethyl]formanilide,
2-(o-aminophenethyl)-1-methylpiperidine,
2'-[2-(1-methyl-2-piperidyl)ethyl]cinnamanilide,
2'-[3-(1-methyl-2-piperidyl)propyl]-p-anisanilide.

The compounds of Formula Ia and Formula Ib are characterized as particularly useful antiserotonin agents as can be demonstrated in the rat uterus. According to this test one of the uterine horns of a rat uterus is suspended in oxygenated salt solution at 30° C. The contractions of this tissue are then recorded and varying concentrations of the test compound introduced into the bath in order to determine the concentration that would decrease the spasmogenic effect of 0.4 microgram per milliliter of serotonin by 50%. This value is designated the $IC_{50}$.

A preferred antiserotonin compound of the present invention is 2'-[2-(1-methyl-2-piperidyl)ethyl]cinnamanilide, which has an $IC_{50}$ of 0.00185 microgram per milliliter. Another preferred substance, 4-methoxy-2'-[2-(1-methyl-2-piperidyl)ethyl]benzanilide, has an $IC_{50}$ of 0.0046 microgram per milliliter. The antiserotonin agents lysergide (LSD) and methysergide have an $IC_{50}$ of 0.012 and 0.0025 microgram per milliliter respectively.

The antiarrhythmic and antiserotonin therapeutic process of the present invention is carried out in mammals by systemic administration of a non-toxic effective dose of the piperidines of Formulas I and XII ranging from about 0.01 to 20 milligram per kilogram of body weight of the mammal or more preferably from 0.1 to 10 mg./kg. Acceptable forms of systemic administration are oral and parenteral. Examples of parenteral administration are intramuscular, intravenous, intraperitoneal, and subcutaneous administration. The dosage of the present therapeutic agents of Formulas I and XII will vary with the form of administration and particular compound chosen. Generally, the compound is administered at a dosage substantially less than the optimum dose of the compound. Thereafter, the dosage is increased by small increments until the optimum effect under the circumstances is reached. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

The antiserotonin activity of 2'-[2-(1-methyl-2-piperidyl)ethyl]-cinnamanilide can also be demonstrated in mice according to the method of S. J. Corne, et al., Brit. J. Pharmacol, 20, 106 (1963). This test is dependent on the metabolism of 5-hydroxytryptophan to serotonin in the brain in mice which are pretreated with a monamine oxidase inhibitor. Depending on the route of administration and the pretreatment time, the following $ED_{50}$ values are obtained; subcutaneous, 4.3 mg./kg. (30 minute pretreatment), 10 mg./kg. (60 minute pretreatment); intraperitoneal, 21 mg./kg. (60 minute pretreatment). These values compare favorably with that obtained with methyldopa, a known serotonin inhibitor, which has an intraperitoneal $ED_{50}$ of 37 mg./kg. (60 minute pretreatment).

When the compounds of this invention characterized by Formulas I and XII are employed as antiserotonin or antiarrhythmic agents they may be administered to mammals alone or in combination with a pharmaceutically acceptable carrier. The proportion of the pharmaceutical carrier is determined by the solubility and chemical nature of the compound and chosen route of administration in standard pharmaceutical practice. For example, they may be administered orally in form of tablets, coated tablets or capsules containing such excipients as starch, milk, sugar, certain types of clay, gelatin, stearic acid or salts thereof, magnesium or calcium stearate, talc, vegetable fats or oils, gums, glycols, and other known excipients. They may be administered orally in the form of solutions which may contain coloring and flavoring agents or they may be injected parenterally, that is intramuscularly, intravenously, or subcutaneously. For parenteral administration they may be used in the form of sterile solution. Said pharmaceutical compositions are prepared by conventional methods.

A recommended dosage unit form comprises a pharmaceutical carrier and the therapeutically active compound in an amount sufficient to provide a non-toxic effective antiserotonin or antiarrhythmic dose ranging from about 0.01 to 20 milligram per kilogram of body weight of the mammal treated.

Advantageously, the compositions can be adapted to supply a fixed dose containing from 1 to 500 mg. and preferably 5 to 100 mg. of the active ingredient.

Preparation of compounds of Formula I according to the process of the present invention is carried out according to Equation 1.

Equation 1.

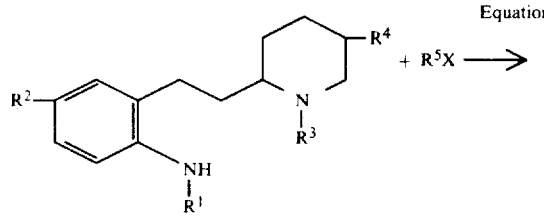

Formula II Formula I + HX wherein $R^1$, $R^2$, $R^4$, and $R^5$ have the meaning stated above and $R^3$ is limited to lower alkyl provided that when $R^5$ is "$R^7$-benzoyl", $R^7$ additionally represents "$NO_2$" but cannot stand for $NH_2$ or OH. Compounds wherein $R^7$ is "$NO_2$" are converted to compounds of Formula I wherein $R^7$ is "$NH_2$" by hydrogenation. Compounds wherein $R^7$ is "acetoxy" are converted to compounds of Formula I wherein $R^7$ is "OH" by hydrolysis. The symbol "X" represents a halogenide of a $R^5$ carbonyl or sulfonyl radical or $R^5X$ taken together represents an anhydride.

Illustrative of $R^5X$ reactants which can be reacted with o-aminophenethylpiperidines of Formula II are:

acetic-formic anhydride,
acetic anhydride,
n-propionic anhydride,
n-butyric anhydride,
isobutyric anhydride,
benzoic anhydride,
acetyl chloride,
propionyl chloride,
butyryl chloride,
methanesulfonyl chloride,
methanesulfonic anhydride,
ethanesulfonic anhydride,
isopropylsulfonyl chloride,
n-butanesulfonyl chloride,
4-methoxybenzoyl chloride,
3,4,5-trimethoxybenzoyl chloride, 3,5-dimethoxybenzoyl chloride,
2-methoxybenzoyl chloride,
2-chlorobenzoyl chloride,
3-acetoxybenzoyl chloride.

In addition $R^5X$ taken together can represent a reactive ester such as, for example, methyl 4-(t-butoxy)benzoate, ethyl picolinate, ethyl propiolate, ethyl 4-dimethylaminobenzoate, ethyl furan-3-carboxylate and the like.

The reaction proceeds when the reactants are contacted and mixed in an inert organic solvent as a reaction medium. Representative inert organic solvents which can be employed as reaction media include ether, benzene, toluene, acetonitrile halogenated hydrocarbons such as chloroform, and the like. Whenever halogenide reactants such as acetyl chloride, etc., are employed, it is desirable to add a hydrogen halide acceptor such as triethylamine to the reaction mixture. Pyridine is preferred particularly as a reaction medium because of its suitability both as a solvent and as an acid acceptor. The temperature at which the reaction is carried out is not critical, although from a convenience and ease of operability viewpoint, room temperature is preferred. The exact proportions of the reactants to be employed is not critical. However, since the o-aminophenethylpiperidines of Formula II and the $R^5X$ reactants are consumed in equimolar proportions, the reactants are preferably employed in such proportions. The reaction is generally complete in about 1 to 24 hr. depending upon the reaction temperature employed. The product can be conveniently separated from the reaction mixture by concentrating the reaction mixture under reduced pressure, dissolving the resulting residue in water and adding thereto a base such as aqueous sodium hydroxide, aqueous sodium carbonate, or aqueous potassium carbonate to make the mixture strongly basic. The product can then be separated by extraction with a halogenated hydrocarbon solvent, ether, benzene, ethyl acetate, etc. Generally, the product can be purified by recrystallization from organic solvents such as isopropyl ether, heptane, methanol, ethanol, isopropyl alcohol, ethyl acetate, water, acetone, and the like, or it can be converted to an acid addition salt. Other means of purification include chromatography, e.g. thin-layer or column.

Conversion of the substances characterized by Formula I and Formula XII to pharmaceutically acceptable acid addition salts is accomplished by admixture of the Formula I and Formula XII bases with substantially one chemical equivalent of any of the various acids hereinbefore defined. Generally the reactions are carried out in an inert solvent. Suitable solvents by way of example, are ethanol, benzene, ethyl acetate, ether, and halogenated hydrocarbons.

Synthesis of the novel o-aminophenethylpiperidine intermediates of Formula II begins with preparation of 2-styrylpyridines of Formula III which are obtained according to the method of L. Horwitz, J. Org. Chem. 21, 1039 (1956) from the reaction of a $R^2$-o-nitrobenzaldehyde and a $R^4$-2-methylpyridine. As shown in Equation 2, the nitro-2-styrylpyridines of Formula III are reduced to an o-aminophenethylpyridine of Formula IV. It is preferred that reduction be carried out catalytically in a solvent employing palladium on carbon catalyst. Suitable solvents by way of example are the lower alkanoyls such as methanol, ethanol, isopropanol, etc.

Equation 2.

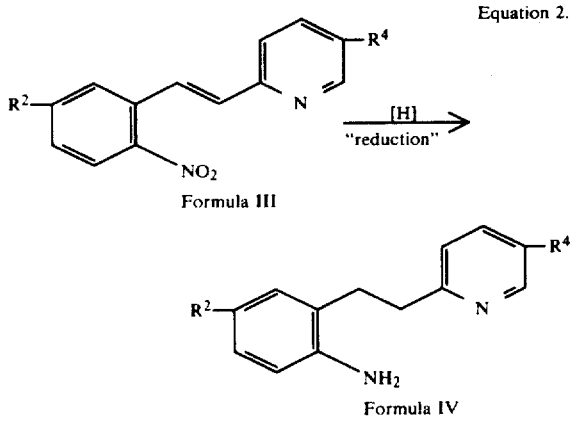

The o-aminophenethylpyridines of Formula IV are then formylated in order to block alkylation of the aromatic amine when the $R^3$ substituent is introduced by quaternization of the pyridine nitrogen with an $R^3$-halide. This conversion of the o-aminophenethylpyridines of Formula IV to the Formula V formyl derivative is illustrated by Equation 3 and is preferably carried out with acetic-formic anhydride.

Equation 3

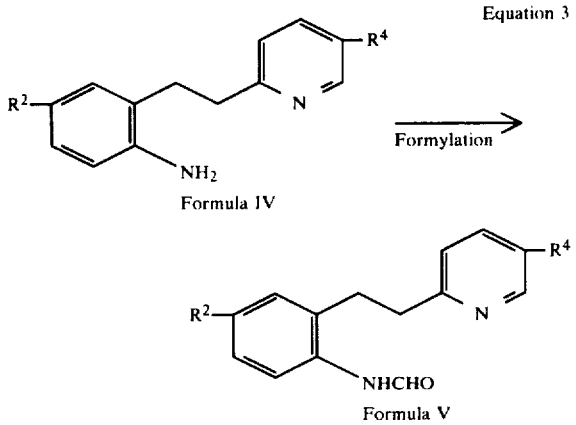

Equation 4 illustrates the alkylation of a Formula V pyridine with an alkyl iodide to provide a pyridinium salt of Formula VI. Depending on the $R^3$ substituent desired, alkyl halides such as ethyl iodide, ethyl bromide, n-propyl iodide, 2-iodopropane, 1-iodobutane, 1-iodo-2-methylpropane, 1-chloro-2-methylpropane, 2-iodo-2-methylpropane and the like are employed. The alkylation is carried out in an inert solvent such as acetone, acetonitrile, etc.

Equation 4

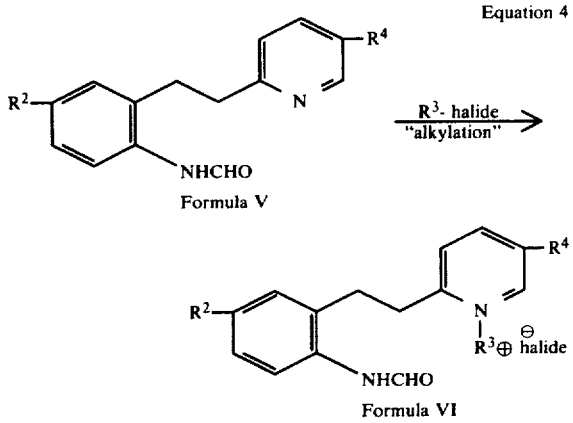

Compounds of Formula VI are converted to the phenethylpiperidines of Formula VII by reduction according to Equation 5. The reduction is carried out catalytically employing platinum as the catalyst in a suitable solvent such as the lower alkanols. The phenethylpiperidines of Formula VII can also be obtained by reduction first with metal borohydrides such as sodium borohydride, or potassium borohydride to provide a tetrahydropyridine which is then further reduced by well known catalytic methods to the piperidines of Formula VII. For example, reduction of 5-diethylcarbamyl-2-(o-formamidophenethyl)-1-methylpyridinium iodide with sodium borohydride in methanol solution provides N,N-diethyl-6-(o-formamidophenethyl)-1-methyltetrahydropyridin-3-carboxamide which is then hydrogenated in ethanol with a 10% palladium on carbon catalyst. It will be recognized that compounds of formula VII represent the products of Formula I of the present invention wherein $R^1$ is a hydrogen and $R^5$ is formyl.

Equation 5.

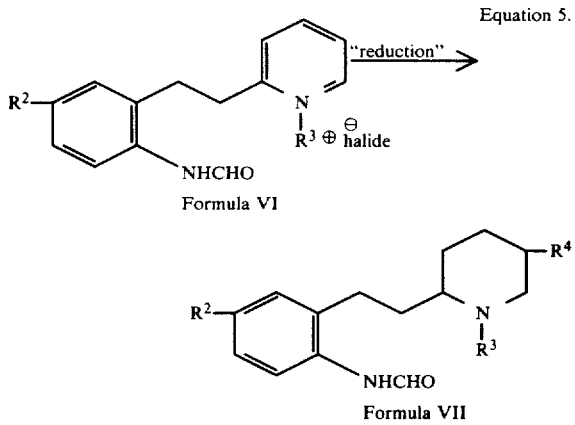

Formula VI

Formula VII

Representative of the formanilides of Formula VII are:

2'-[2-(1-methyl-2-piperidyl)ethyl]formanilide,
2'-[2-(5-methyl-1-methyl-2-piperidyl)ethyl]formanilide,
2'-[2-(5-n-butyl-1-methyl-2-piperidyl)ethyl]-formanilide,
2'-[2-(1-isopropyl-2-piperidyl)ethyl]formanilide,
2'-[2-(1-n-butyl-2-piperidyl)ethyl]formanilide,
4'-methoxy-2'-[2-(1-methyl-2-piperidyl)ethyl]-formanilide,
4'-n-butoxy-2'-[2-(1-methyl-2-piperidyl)ethyl]-formanilide,
4'-isopropoxy-2'-[2-(5-isopropyl-1-methyl-2-piperidyl-)ethyl]formanilide,
N,N-dimethyl-6-(o-formamidophenethyl)-1-methylpiperidine-3-carboxamide,
N,N-diethyl-6-(o-formamidophenethyl)-1-methylpiperidine-3-carboxamide,
N,N-di-n-butyl-6-(o-formamidophenethyl)-1-methylpiperidine-3-carboxamide,
N,N-diethyl-6-[(2-formamido-5-methoxyphenethyl)-1-methylpiperidine-3-carboxamide.

If the o-aminophenethylpyridines of Formula IV are acylated with alkanoyl halides such as acetyl chloride, propionyl chloride, isobutyryl chloride, butyryl chloride and the like, and the sequence of reactions illustrated by Equations 3–5 repeated, products of Formula I are obtained wherein $R^1$ is hydrogen and $R^5$ is alkanoyl. Representative of the alkanoylanilides of Formula I thus formed are:

2'-[2-(1-methyl-2-piperidyl)ethyl]acetanilide,
4'-methoxy-2'-[2-(1-methyl-2-piperidyl)ethyl]-acetanilide,
2'-[2-(1-n-butyl-2-piperidyl)ethyl]acetanilide,
2'-[2-(5-ethyl-1-methyl-2-piperidyl)ethyl]acetanilide,
N,N-diethyl-6-(o-acetamidophenethyl)-1-methylpiperidine-3-carboxamide,
2'-[2-(1-methyl-2-piperidyl)ethyl]butyranilide,
2'-[2-(1-methyl-2-piperidyl)ethyl]-2-methylpropionanilide,
4'-n-butoxy-2'-[2-(1-methyl-2-piperidyl)ethyl]-proprionanilide, Acid hydrolysis of the formanilides of Formula VII or the analogous alkanoylanilides provide o-aminophenethylpiperidine intermediates of Formula II wherein $R^1$ is hydrogen. Representative of o-aminophenethylpiperidines which can be obtained in this manner are:

2-(o-aminophenethyl)-1-methylpiperidine,
2-(o-aminophenethyl)-1,5-dimethylpiperidine,
2-(o-aminophenethyl)-5-ethyl-1-methylpiperidine,
2-(o-aminophenethyl)-5-n-butyl-1-methylpiperidine,
2-(o-aminophenethyl)-1-isopropylpiperidine,
2-(o-aminophenethyl)-n-butylpiperidine,
2-(2-amino-5-methoxyphenethyl)-1-methylpiperidine,
2-(2-amino-5-n-butoxyphenethyl)-1-methylpiperidine,
2-(2-amino-5-isopropoxyphenethyl)-1-methylpiperidine,
6-(o-aminophenethyl)-N,N-dimethyl-1-methylpiperidine-3-carboxamide,
6-(o-aminophenethyl)-N,N-diethyl-1-methylpiperidine)-3-carboxamide,
6-(o-aminophenethyl)-N,N-di-n-butyl-1-methylpiperidine-3-carboxamide,
6-(2-amino-5-methoxyphenethyl)-N,N-diethyl-1-methylpiperidine-3-carboxamide.

Reduction of some of the compounds of Formula VII with lithium aluminum hydride provide o-aminophenethylpiperidine intermediates of Formula II wherein $R^1$ is alkyl. Representative of o-(N-alkylaminophenethyl)-piperidines which can be obtained in this manner are:

2-(o-methylaminophenethyl)-1-methylpiperidine,
2-(o-methylaminophenethyl)-1,5-dimethylpiperidine,
2-(o-methylaminophenethyl)-5-ethyl-1-methylpiperidine,
2-(o-methylaminophenethyl)-5-n-butyl-1-methylpiperidine,
2-(o-methylaminophenethyl)-1-isopropylpiperidine,
2-(o-methylaminophenethyl)-1-n-butylpiperidine,
2-(2-methylamino-5-methoxyphenethyl)-1-methylpiperidine,
2-(2-methylamino-5-n-butoxyphenethyl)-1-methylpiperidine,
2-(2-methylamino-5-isopropoxyphenethyl)-1-methylpiperidine,
2-(o-ethylaminophenethyl)-1-methylpiperidine,
2-(2-ethylamino-5-methoxyphenethyl)-1-methylpiperidine,
2-(2-ethylaminophenethyl)-1-n-butylpiperidine,
2-(2-ethylaminophenethyl)-5-ethyl-1-methylpiperidine,
2-(2-n-butylaminophenethyl)-1-methylpiperidine,
2-(2-isobutylaminophenethyl)-1-methylpiperidine,
2-(2-n-propylamino-5-n-butoxyphenethyl)-1-methylpiperidine.

An alternate method for the preparation of compounds of Formula II wherein $R^1$ is hydrogen is depicted in Equation 6.

Equation 6.

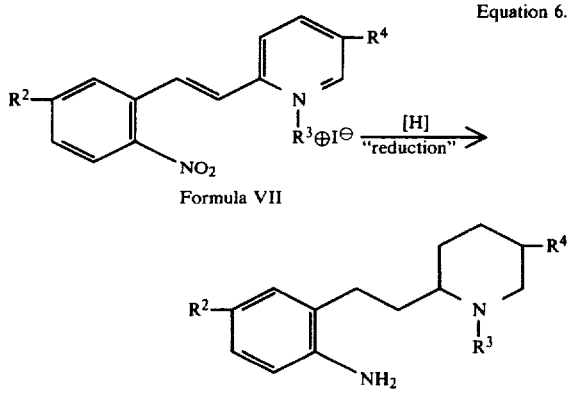

Formula VII

Formula IX

Pyridinium iodides of Formula VIII prepared from the corresponding aromatic aldehyde and the 2-alkylpyridinium salt according to the method of L. Horwitz, J. Org. Chem. 21, 1039 (1956) are reduced according to the method of A. P. Phillips, J. Am. Chem. Soc. 72, 1850 (1950). Preferably the catalytic reduction is carried out employing a platinum catalyst in methanol solution.

An alternate method for the preparation of compounds of Formula II wherein $R^1$ is alkyl is depicted in Equation 7.

Equation 7.

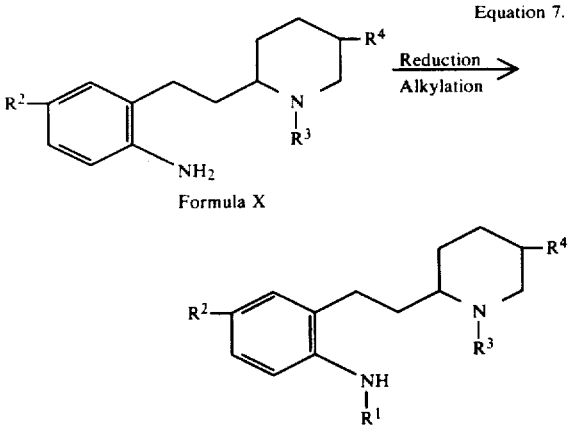

Formula X

Formula XI

Reductive alkylation of o-aminophenethylpiperidines of Formula X with an aldehyde such as acetaldehyde, propionaldehyde, n-butyraldehyde, isobutyraldehyde, or a ketone such as acetone or butanone provide $R^1$-aminophenethylpiperidines of Formula XI. This method is well known to those skilled in the art, refer to Synthetic Organic Chemistry, Wagner and Zook, Wiley, 1953, page 662.

Compounds of Formula I and Formula XII wherein $R^3$ and $R^8$ are hydrogen, lower alkyl, or $R^5$ or $R^9$ are isonipecotoyl are obtained by catalytic reduction of the corresponding pyridyl compounds. For example, reduction of 2'-[2-(2-pyridyl)ethyl]-p-anisanilide employing a palladium on carbon catalyst provides 2'-[-2-(2-piperidyl)ethyl]-p-anisanilide. Similarly, reduction of 2'-[2-(1-methyl-2-piperidyl)ethyl]isonicotanilide affords 2'-[2-(1-methyl-2-piperidyl)ethyl]isonipecotoicanilide.

Compounds of Formula XII (illustrated by Formula XV) wherein the divalent radical "A" is

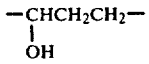

and $R^8$ is lower alkyl can also be obtained by reaction of an o-formylanilide of Formula XIII with a 2-(N-$R^8$-2-piperidyl)ethyl magnesium chloride of Formula XIV as depicted by Equation 8.

Equation 8.

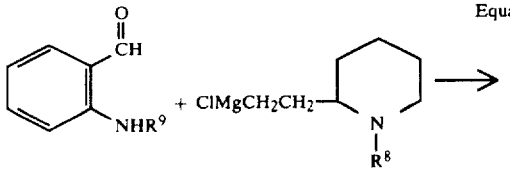

Formula XIII Formula XIV

-continued

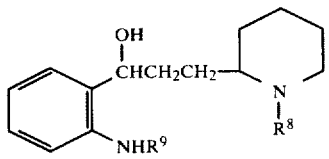

Formula XV

The following examples illustrate the best mode contemplated for carrying out the present invention. They are merely illustrative and are not to be construed as limiting the scope of the claims in any manner whatsoever.

EXAMPLES OF SPECIFIC EMBODIMENTS

EXAMPLE 1

2-(O-Aminophenethyl)-1-methylpiperidine

A suspension of 2-(o-nitrostyryl)-1-methylpyridinium iodide (40.5 mg., 0.11 mole) prepared according to the method of L. Horwitz, J. Org. Chem., 21, 1039 (1956) in 200 ml. of ethanol is hydrogenated in a Parr hydrogenation apparatus employing 0.3 g. of platinum oxide catalyst while maintaining a reaction temperature of from about 50° to 74° C. When the hydrogen uptake ceases (about 3 hours), the reduction mixture is filtered, the filtrate evaporated and the resulting residue taken up in 500 ml. of water. The aqueous solution is basified with 40% sodium hydroxide and extracted with several 200 ml. portions of ether. Ethereal extracts are combined, washed with water, dried over magnesium sulfate, and the ether evaporated. Distillation of the residue thus obtained provides 20.8 g. (87% yield) of 2-o-aminophenethyl)-1-methylpiperidine base having a boiling point of 121°-125° C. at 0.04 mm.

Analysis Calcd. for $C_{14}H_{22}N_2$: C, 77.01; H, 10.16; N, 12.83. Found: C, 76.68; H, 9.83; N, 12.76.

Treating the base with ethanolic hydrogen chloride in ethanol provides 2-(o-aminophenethyl)-1-methylpiperidine dihydrochloride (crystallized from methanol-isopropyl ether), m.p. 268.5°-271.5° C. (corr.).

Analysis. Calcd. for $C_{14}H_{24}Cl_2N_2$: C, 57.73; H, 8.31; N, 9.62. Found: C, 57.67; H, 8.22; N, 9.60.

2-(o-Aminophenethyl)-1-methylpiperidine has antiarrhythmic properties having an $EC_{50}$ of 44 microgram per milliliter in the hereinabove described rabbit atrium test.

EXAMPLE 2

2-(o-Methylaminophenethyl)-1-methylpiperidine a. 2-(o-Aminophenethyl)pyridine.

A solution of 2-(o-nitrostyryl)pyridine (94.3 g., 0.42 mole) in 400 ml. of ethanol is reduced on a Parr hydrogenation apparatus employing 2 g. of 10% palladium on carbon catalyst to provide 2-(o-aminophenethyl)pyridine, m.p. 59°-61° C. The isolation of the pyridine product is carried out in the usual manner by collecting the catalyst and evaporating the ethanolic solvent.

b. 2-(o-Formamidophenethyl)pyridine

An aceticformic anhydride mixture is prepared by mixing acetic anhydride (140 ml.) and formic acid (70 ml.). To this mixture, 2-(o-aminophenethyl)pyridine (59 g., 0.3 mole) is added in one portion with vigorous stirring at 25° C. After 15 minutes the solution is diluted with 450 ml. of water and concentrated in vacuo. The resulting residue is taken up in 1 liter of water and made basic with 50% sodium hydroxide. The basified solution is extracted with chloroform, the chloroform extract washed with water, dried over magnesium sulfate and the chloroform solvent evaporated. Crystallization of the residue from isopropyl acetate provides 57 g. (83% yield) of 2-(o-formamidophenethyl)pyridine melting at 78°-81° C. (uncorrected). An analytical sample (from isopropyl acetate) has a melting point of 83°-83.5° C. (corr.).

Analysis. Calcd. for $C_{14}H_{14}N_2O$: C, 74.31; H, 6.24; N, 12.38. Found: C, 74.56; H, 6.25; N, 12.45.

c. 2-(o-Formamidophenethyl)-1-methylpyridinium iodide.

A solution of 2-(o-formamidophenethyl)pyridine (55 g., 0.243 mole) and methyl iodide (38 g., 0.268 mole) in 500 ml. of acetone is refluxed for 20 hours. The mixture is cooled at 5° C. and filtered to provide 82 g. (92%) of the pyridinium iodide having melting point of 199.5°-201.5° C.

Analysis. Calcd. for $C_{15}H_{17}IN_2O$: C, 48.92; H, 4.65; N, 7.61. Found: C, 48.74; H, 4.83; N, 7.65.

d. 2'-[2-(1-Methyl-2-piperidyl)ethyl]formanilide.

Reduction of 2-(o-formamidophenethyl)-1-methylpyridinium iodide as described in Example 1 for 2-(o-nitrostyryl)-1-methylpyridinium iodide provides 2'-[2-(1-methyl-2-piperidyl)-ethyl]formanilide which is purified by crystallization from isopropyl ether, (79% yield) m.p. 81°-84.5° C. (corr.).

Analysis. Calcd. for $C_{15}H_{22}N_2O$: C, 73.13; H, 9.00; N, 11.37. Found: C, 73.12; H, 8.75; N, 11.31.

e. 2-(o-Methylaminophenethyl)-1-methylpiperidine

A solution of 2'-[2-(1-methyl-2-piperidyl)ethyl]formanilide (20 g., 0.0815 mole) in 100 ml. of tetrahydrofuran is added dropwise to a stirred mixture of lithium aluminum hydride (4.4 g., 0.11 mole) in 100 ml. of tetrahydrofuran. The mixture is refluxed for 75 minutes, cooled, and hydrolyzed by the sequential addition of 4.4 ml. or water, 4.4 ml. of 15% sodium hydroxide and then 13.2 ml. of water. The hydrolyzed mixture is filtered, the filter cake washed with a 50 ml. portion of tetrahydrofuran and the filtrate concentrated in vacuo. The residue thus obtained is distilled to provide 16.6 g. of 2-(o-methylaminophenethyl)-1-methylpiperidine having a boiling point of 150°-155° C. at 0.05 mm. Hg.

EXAMPLE 3

2-(2-Amino-5-methoxyphenethyl)-1-methylpiperidine a. 2'-(2-Amino-5-methoxyphenethyl)pyridine.

Reduction of 2-(2-nitro-5-methoxystyryl)pyridine as described in Example 2 (a) for 2-(o-nitrostyryl)pyridine provides 2-(2-amino-5-methoxyphenethyl)pyridine having a melting point of 77.5°-78.5° C. (corr.) as the monohydrate obtained by crystallization from isopropyl acetate-ethanol-water.

Analysis. Calcd. for $C_{14}H_{16}N_2O.H_2O$: C, 68.27; H, 7.37; N, 11.37. Found: C, 68.04; H, 7.30; N, 11.30.

b. 2-(2-Formamido-5-methoxyphenethyl)pyridine.

Formylation of 2-(2-amino-5-methoxyphenethyl)pyridine as described in Example 2 (b) for 2-(o-aminophenethyl)pyridine provides a 71% yield of 2-(2-formamido-5-methoxyphenethyl)pyridine. An analytical sample obtained by crystallization from isopropyl acetate has a melting point of 93.5°-94° C. (corr.).

Analysis. Calcd. for $C_{15}H_{16}N_2O_2$: C, 70.29; H, 6.29; N, 10.93. Found: C, 70.28; H, 6.51; N, 10.98.

c. 2-(2-Formamido-5-methoxyphenethyl)-1-methylpyridinium iodide.

The pyridinium iodide is obtained by treating 2-(2-formamido-5methoxyphenethyl)pyridine with methyl iodide according to the procedure described in Example 2 (c) for 2-(o-formamidophenethyl)pyridine. Analytically pure 2-(2-formamido-5-methoxyphenethyl)-1-methylpyridium iodide is obtained in a yield of 95% and has a melting point of 184°-186.5° C. (corr.).

Analysis. Calcd. for $C_{16}H_{19}IN_2O_2$: C, 48.25; H, 4.81; N, 7.04. Found: C, 48.18; H, 4.84; N, 7.16.

d. 2-(2-Amino-5-methoxyphenethyl)-1-methylpiperidine.

Catalytic reduction of 2-(2-formamido-5-methoxyphenethyl)-1-methylpyridinium iodide as described in Example 1 for 2-(o-nitrostyryl)-1-methylpyridinium iodide provides 2-(2-formamido-5-methoxyphenethyl)-1methylpiperidine. This material is deformylated in 1 N methanolic hydrogen chloride providing 2-(2-amino-5-methoxyphenethyl)-1-methylpiperidine.

Another method of preparing 2-(2-formamido-5-methoxyphenethyl)-1-methylpiperidine is to reduce 2-(2-formamido-5-methoxyphenethyl)-1-methylpyridinium iodide first with sodium borohydride to provide 2-(2-formamido-5-methoxyphenethyl)-1-methyltetrahydropyridine which is then reduced catalytically with palladium on carbon. This procedure is described in Example 4 (d).

EXAMPLE 4

6-(o-Aminophenethyl)-N,N-diethyl-1-methylpiperidine-3-carboxamide (Racemate A and Racemate B)

a. N,N-Diethyl-6-(o-nitrostyryl)nicotinamide.

Reaction of o-nitrobenzaldehyde (41.7 g., 0.276 mole) with N,N-diethyl-6-methylnicotinamide (53.1 g., 0.276 mole) in the presence of acetic anhydride (56.3 g., 0.552 mole) according to the method of L. Horwitz, J. Org. Chem., 21,.1039 (1956) provides 67.4 g. (75%) of N,N-diethyl-6-(o-nitrostyryl)-nicotinamide. Crystallization from acetonitrile affords the analytically pure nicotinamide having a melting point of 145°-147° C. (corr.).

Analysis. Calcd. for $C_{18}H_{19}N_3O_3$: C, 66.44; H, 5.89; N, 12.92 Found: C, 66.62; H, 6.01; N, 12.68.

b. 6-(o-Aminophenethyl)-N,N-diethylnicotinamide.

N,N-diethyl-6-(o-nitrostyryl)nicotinamide (16.3 g., 0.05 mole) reduced in 150 ml. of ethanol employing 0.1 g. of 10% palladium on carbon catalyst according to the procedure described in Example 2 (a) for 2(o-aminophenethyl)pyridine provides 6-(o-aminophenethyl)-N,N-diethylnicotinamide base. Addition of ethanolic hydrogen chloride to the nicotinamide base in ethanol provides 6-(o-aminophenethyl)-N,N-diethylnicotinamide dihydrochloride, m.p. 224°-226° C. (corr.).

Analysis. Calcd. for $C_{18}H_{25}Cl_2N_3O$: C, 58.38; H, 6.80; N, 11.35. Found: C, 58.21; H, 6.86; N, 11.31.

c. 5-Diethylcarbamyl-2-(o-formamidophenethyl)-1-methylpyridinium iodide.

Formylation of 6-(o-aminophenethyl)-N,N-diethylnicotinamide as described in Example 2 (b) for 2-(o-formamidophenethyl)pyridine provides 6-(o-formamidophenethyl)-N,N-diethylnicotinamide which is then methylated as described in Example 2 (c) for 2-(o-formamidophenethyl)-1-methylpyridinium iodide to provide 5-diethylcarbamyl-2-(o-formamidophenethyl)-1-methylpyridinium iodide. This product is employed in the following step without further purification.

d. N,N-Diethyl-6-(o-formamidophenethyl)-1-methylpiperidine-3-carboxamide.

A 50% sodium hydroxide solution (9.6 g., 0.12 mole) in 45 ml. of water is added to a solution of 5-diethylcarbamyl -2-(o-formamidophenethyl)-1-methylpyridinium iodide (46.7 g., 0.1 mole) in 300 ml. of methanol. Sodium borohydride (4.56 g., 0.12 mole) is added in portions with stirring to the reaction mixture. After 2 hr. the mixture is evaporated and water (500 ml.) is added to the resulting residue. This mixture is extracted with ether, the ethereal extracts washed with water, dried over magnesium sulfate and the other evaporated. The resulting residue consisting of N,N-diethyl-6-(o-formamidophenethyl)-1-methyltetrahydropyridine-3-carboxamide hydrogenated in a Parr apparatus in 200 ml. of ethanol employing 4 g. of 10% palladium on carbon as the catalyst at a temperature of 50°-70° C. provides N,N-diethyl-6-(o-formamidophenethyl)-1-methylpiperidine-3-carboxamide.

e. 6-(o-Aminophenethyl)-N,N-diethyl-1-methylpiperidine-3-carboxamide.

N,N-Diethyl-6-(o-formamidophenethyl)-1-methylpiperidine-3-carboxamide is hydrolyzed to 6-(o-aminophenethyl)-N,N-diethyl-1-methylpiperidine-3-carboxamide as described in Example 3 (d) for 2-(o-methylaminophenethyl)-1-methylpiperidine.

f. Separation of 6-(o-aminophenthyl)-N,N-diethyl-1-methylpiperidine-3-carboxamide into Racemate A and Racemate B.

Crude 6-(o-aminophenethyl)-N,N-diethyl-1-methylpiperidine-3-carboxamide (11 g.) containing a 1:1 mixture of Racemate A and Racemate B which is obtained in the preceding steps by hydrolysis of N,N-diethyl-6-(o-formamidophenethyl)-1-methylpiperidine-3-carboxamide is dissolved in 50 ml. of benzene and loaded on a 4 cm. diameter chromatographic column packed to a height of 45 cm. with silica gel (300 g., 100-200 mesh). The column is eluted with the following solvent combinations and 100 ml. fractions collected: fractions 1-2, benzene; fractions 3-39, ethyl acetate-ethanol 7:3 plus 0.2% of 58% ammonium hydroxide; fractions 40-70, ethyl acetate-ethanol 1:1 plus 0.5% of 58% ammonium hydroxide; fractions 71-78, ethanol plus 0.5% of 58% ammonium hydroxide. Fractions 13 through 44 are combined and concentrated to provide about 4 to 5 g. of pure Racemate A as an oil. Evaporation of combined fractions 55-72 provides 3.2 g. of pure Racemate B as an oil.

EXAMPLE 5

2-(o-Aminophenethyl)-5-ethyl-1-methylpiperidine (Racemate A and Racemate B)

a. 5-Ethyl-2-(o-nitrostyryl)pyridine

Reaction of o-nitrobenzaldehyde (100 g., 0.66 mole) with 5-ethyl-2-methylpyridine (80 g., 0.66 mole) in the presence of acetic anhydride (135 g., 1.32 mole) according to the method of L. Horwitz, J. Org. Chem., 21, 1039 (1956) provides 54.4 g. (32%) of 5-ethyl-2-(o-nitrostyryl)pyridine. An analytical sample obtained by crystallization from isopropyl ether has a melting point of 52.5°-54.5° C. (corr.).

Analysis. Calcd. for $C_{15}H_{14}N_2O_2$: C, 70.85; H, 5.55; N, 11.02. Found: C, 71.01; H, 5.40; N, 10.96.

b. 2(o-Aminophenethyl)-5-ethylpyridine.

Reduction of 5-ethyl-2-(o-nitrostyryl)pyridine as described in Example 2 (a) for 2-(o-nitrostyryl)pyridine provides 2-(o-aminophenethyl)-5-ethylpyridine having a melting point of 52.5°-53.5° C. (corr.) when crystallized from isopropyl ether-heptane.

c. 5-Ethyl-2-(o-formamidophenethyl)pyridine.

Reaction of 2-(o-aminophenethyl)-5-ethylpyridine with acetic anhydride and formic acid according to the procedure described in Example 2 (b) for 2-(o-aminophenethyl)pyridine provides the formylated product 5-ethyl-2-(o-formamidophenethyl)pyridine which can be crystallized from isopropyl ether, m.p. 62°-63.5° C. (corr.).

Analysis. Calcd. for $C_{16}H_{18}N_2O$: C, 75.56; H, 7.13; N, 11.02. Found: C, 75.53; H, 7.07; N, 10.96.

d. 5-Ethyl-2-(o-formamidophenethyl)-1-methylpyridinium iodide.

Reaction of 5-ethyl-2-(o-formamidophenethyl)pyridine with methyl iodide in acetone according to the procedure of Example 2 (c) for 2-(o-formamidophenethyl)pyridine provides a 74% yield of analytically pure 5-ethyl-2-(o-formamidophenethyl)-1-methylpyridinium iodide having a melting point of 134.5°-136.5° C.

Analysis. Calcd. for $C_{17}H_{21}IN_2O$: C, 51.53; H, 5.34; N, 7.07. Found: C, 51.79; H, 5.35; N, 6.84.

e. 5-Ethyl-b 2-(o-formamidophenthyl)-1-methylpiperidine.

Reduction of 5-ethyl-2-(o-formamidophenethyl)-1-methylpyridium iodide as described in Example 4 (d) for the corresponding N,N-diethyl-3-carboxamide provides 5-ethyl-2-(o-formamidophenethyl)-1-methylpiperidine comprised of a 1:1 mixture of Racemate A and Racemate B.

f. Separation of 2-(o-aminophenethyl)-5-ethyl-1-methylpiperidine into Racemate A and Racemate B.

Racemate B is isolated from the Racemate A and B mixture of 5-ethyl-2-(o-formamidophenethyl)-1-methylpiperidine by treating 19.8 g. of the mixture with oxalic acid (9.15 g., 0.0723 mole) dihydrate in 200 ml. of ethanol which provides 14.3 g. of a crystalline solid (oxalic acid salt), m.p. 166°-170° C. Crystallization of this material from ethanol selectively provides 8.2 g., of the Racemate B of 2-(o-formamidophenethyl)-5-ethyl-1-methylpiperidine as the oxalic acid salt, m.p. 174°-176° C.

Analysis. Calcd. for $C_{17}H_{26}N_2O.C_2H_2O_4$: C, 62.62; H, 7.74; N, 7.69. Found: C, 62.45; H, 7.46; N, 7.76.

The oxalic acid salt of 2-(o-formamidophenethyl)-5-ethyl-1-methylpiperidine (Racemate B) is converted to the free base by treatment with potassium hydroxide.

Hydrolysis of the formamido free base is carried out by stirring with 125 ml. of 1 N methanolic hydrogen chloride for 24 hr. Concentration of the methanolic mixture in vacuo provides a residue which is taken up in water and made basic with 50% sodium hydroxide. Extraction of the basified mixture with ether and concentration of the ether extract provides 5.5 g. of 2-(o-aminophenethyl)-5-ethyl-1-methylpiperidine B Racemate free base.

The oxalic acid salt mother liquor remaining from isolation of 2-(o-formamidophenethyl)-5-ethyl-1-methylpiperidine (Racemate B) which is enriched in 2-(o-formamidophenethyl)-5-ethyl-1-methylpiperidine (Racemate A) is converted to the free base. Deformylation of 6.7 g. of the 5-ethyl-2-(o-formamidophenethyl)-1-methylpiperidine base in 250 ml. of 1 N methanolic hydrogen chloride provides 5.1 g. of hydrochloric acid salt, m.p. 235°-238° C. This salt selectively crystallized from ethanol-isopropyl ether provides 4.4 g. of material which is then converted to the free base providing 3.3 g.

of 2-(o-aminophenethyl)-5-ethyl-1-methylpiperidine (Racemate A) as an oil.

EXAMPLE 6

2-(o-Isopropylaminophenethyl)-1-methylpiperidine

A mixture of 0.01 mole of 2-(o-aminophenethyl)-1-methylpiperidine, 2.40 ml. (0.03 mole) of acetone, 0.63 ml. (0.01 mole) of acetic acid, and 0.25 g. of platinum oxide in 100 ml. of absolute ethanol is hydrogenated at 40 p.s.i. until 0.01 mole of hydrogen has been absorbed. The reaction mixture is filtered, the filtrate acidified with ethanolic hydrogen chloride and evaporated to dryness at reduced pressure to provide 2-(o-isopropylaminophenethyl)-1-methylpiperidine as a dihydrochloride salt. Alternatively, the reaction mixture can be filtered, and concentrated to provide the 2'-(o-isopropylaminophenethyl)-1-methylpiperidine as an acetate salt.

In a similar manner by employing other o-aminophenethylpiperidines, other 2-(o-alkylaminophenethyl)-1-methylpiperidines can be prepared.

The free base is isolated from either the hydrochloric acid or acetate addition salt by standard procedures well known to those skilled in the art. For example, the dihydrochloride salt of 2-(o-isopropylaminophenethyl)-1-methylpiperidine is dissolved in water, neutralized with sodium hydroxide. The free base is extracted from the mixture with an immiscible solvent such as ether or ethyl acetate. Concentration of the extracted mixture provides the isolated free base.

EXAMPLE 7-24

Additional o-aminophenthylpiperidines

By employing the procedures of Examples 1-6, other o-aminophenethylpiperidines which are useful for the preparation of the compounds of Formula I are obtained. Representative of the o-aminophenethylpiperidines of the present invention are listed in Table I, along with starting materials and reference to the experiment number wherein the procedure is described. It will be readily apparent to those skilled in the art that in many instances, a particular o-aminophenethylpiperidine can be prepared by more than one procedure. Thus, for example 2-(o-aminophenethyl)-1-methylpiperidine obtained in Example 1 can be prepared according to the method of Example 3 by hydrolyzing 2'-[2-(2-methyl-2-piperidyl)ethyl]formanilide which is obtained from 2-(o-nitrostyryl)piperidine.

TABLE I

ADDITIONAL o-AMINOPHENETHYLPIPERIDINES

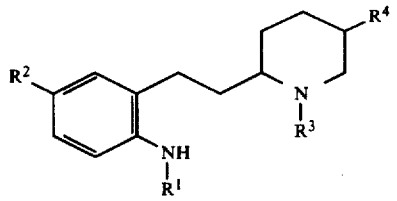

| Example | $R^1$ | $R^2$ | $R^3$ | $R^4$ | Starting Materials | Procedure (Example No.) |
|---|---|---|---|---|---|---|
| 7 | H | H | $CH_3$ | $CH_3$ | 2,5-dimethylpyridine and o-nitrobenzaldehyde | 5 |
| 8 | H | H | $CH_3$ | n-$C_4H_9$ | 5-n-butyl-2-methylpyridine and o-nitrobenzaldehyde | 5 |
| 9 | H | H | $CH_3$ | $(CH_3)_2CH$ | 5-isopropyl-2-methylpyridine and o-nitrobenzaldehyde | 5 |
| 10 | H | $(CH_3)_2CHO$ | $CH_3$ | $CH(CH_3)_2$ | 5-isopropyl-2-methylpyridine and 2-nitro-5-isopropoxybenzaldehyde | 5 |
| 11 | H | H | $CH_3$ | $CON(CH_3)_2$ | o-nitrobenzaldehyde and N,N-dimethyl-6-methylnicotinamide | 4 |
| 12 | H | H | $CH_3$ | $CON(n\text{-}C_4H_9)_2$ | o-nitrobenzaldehyde and N,N-di(n-butyl)-6-methylnicotinamide | 4 |
| 13 | H | $CH_3O$ | $CH_3$ | $CH_3$ | 2,5-dimethylpyridine and 2-nitro-5-methoxybenzaldehyde | 5 |
| 14 | H | n-$C_4H_9O$ | $CH_3$ | H | 2-methylpyridine, 2-nitro-5-n-butoxybenzaldehyde and methyl iodide | 3 |
| 15 | H | H | n-$C_4H_9$ | H | 2-methylpyridine, o-nitrobenzaldehyde and 1-iodobutane | 3 |
| 16 | H | H | $(CH_3)_3C$ | H | 2-methylpyridine, o-nitrobenzaldehyde and 1-iodo-2-methylpropane | 3 |
| 17 | H | $CH_3O$ | $(CH_3)_2CH$ | H | 2-methylpyridine, 2-nitro-5-methoxybenzaldehyde and 2-iodopropane | 3 |
| 18 | $CH_3$ | H | $CH_3$ | $CH_3$ | 2,5-dimethylpyridine, o-nitrobenzaldehyde | 2 |
| 19 | n-$C_4H_9$ | H | $CH_3$ | H | 2-methylpyridine, o-nitrobenzaldehyde and butyryl chloride | 2 |
| 20 | $CH_3$ | $CH_3O$ | $CH_3$ | H | 2-methylpyridine and 2-nitro-5-methoxybenzaldehyde | 2 |
| 21 | H | H | $(CH_3)_2CH$ | H | 1-isopropyl-2-methylpyridinium iodide and o-nitrobenzaldehyde | 1 |
| 22 | $C_2H_5$ | H | $CH_3$ | H | 2-(o-aminophenethyl)-1-methylpiperidine and acetaldehyde | 6 |
| 23 | $(CH_3)_2CH$ | $CH_3O$ | $CH_3$ | H | 2-(2-amino-5-methoxyphenethyl)-1-methylpiperidine and acetone | 6 |
| 24 | $CH_3$ | $CH_3O$ | $CH_3$ | $C_2H_5$ | 5-ethyl-2-methylpyridine and 2-nitro-5-methoxybenzaldehyde | 2 |

EXAMPLE 25

2'-[2-(1-Methyl-2-piperidyl)ethyl]-cinnamanilide

Cinnamoyl chloride (6.0 g., 0.036 mole) is added to a solution of 2-(o-aminophenethyl)-1-methylpiperidine (7.8 g., 0.036 mole) in 100 ml. of pyridine in one portion with vigorous stirring. Stirring is continued for 3 hours and the pyridine solution is then concentrated in vacuo. The resulting residue is taken up to 150 ml. of water and made basic with 40% sodium hydroxide. The basified solution is extracted with several 200 ml. portions of ether, which are combined, washed with water, dried over magnesium sulfate and the ether solvent evaporated. The residue thus obtained crystallizes and is further purified by crystallizing from isopropyl ether providing 8.7 g. (70% yield) of analytically pure 2'-[2-(1-methyl-2-piperidyl)ethyl]cinnamanilide melting at 101.5°-103.5° C. (corr.).

Analysis. Calcd. for $C_{23}H_{28}N_2O$: C, 79.27; H, 8.10; N, 8.04. Found: C, 79.24; H, 8.35; N, 8.09.

EXAMPLE 26

2'-[2-(1-Methyl-2-piperidyl)ethyl]-α-methylcinnamanilide mucate

By substituting a molar equivalent of α-methylcinnamoyl chloride in lieu of cinnamoyl chloride in Example 25, the substituted phenethylpiperidine free base is obtained. The mucate salt is prepared by dissolving the free base in methanol and adding mucic acid to the methanolic solution until the solid mucic acid no longer dissolves. Undissolved mucic acid is removed by filtering and the filtrate concentrated. The residue which remains in crystallized from ethanol-ethyl acetate to provide analytically pure 2'-[2-(1-methyl-2-piperidyl)ethyl]-α-methylcinnamanilide mucate having a melting point of 154.5°-156.5° C. (dec.) (corr.).

Analysis. Calcd. for $C_{24}H_{30}N_{20}.\frac{1}{2}C_6H_{10}O_8$: C, 69.35; H, 7.54; N, 5.99. Found: C, 69.25; H, 7.59; N, 5.89.

EXAMPLE 27

N-Methyl-2'-[2-(1-methyl-2-piperidyl)-ethyl]cinnamanilide mucate

By substituting a molar equivalent of 2-(o-methylaminophenethyl)-1-methylpiperidine in lieu of 2-(o-aminophenethyl)-1-methylpiperidine in Example 25, N-methyl-2'-[2-(methyl-2-piperidyl)ethyl]cinnamanilide is obtained. The mucate salt is prepared according to Example 26, and is crystallized from methanol to provide analytically pure N-methyl-2'-[2-(1-methyl-2-piperidyl)ethyl]cinnamanilide mucate in 38% yield having a melting point of 174°-176° C. (corr.).

Analysis. Calcd. for $C_{24}H_{30}N_2O.\frac{1}{2}C_6H_{10}O_8$: C, 69.35; H, 7.54; N, 5.99. Found: C, 69.38; H, 7.56; N, 5.97.

EXAMPLE 28

4'-Methoxy-2'-[2-(1-methyl-2-piperidyl)-ethyl]cinnamanilide

By substituting a molar equivalent of 2-(2-amino-5-methoxyphenethyl)-1-methylpiperidine in lieu of 2-(o-aminophenethyl)-1-methylpiperidine in Example 25, the phenethylpiperidine free base is obtained. Analytically pure 4'-methoxy-2'-[2-(1-methyl-2-piperidyl)ethyl]cinnamandilide is obtained by crystallizing the crude free base from isopropyl acetate and has a melting point of 126.5°-127.5° C. (corr.).

Analysis. Calcd. for $C_{24}H_{30}N_2O_2$: C, 76,15; H, 7.99; N, 7.40. Found: C, 76.37; H, 7.93; N, 7.36.

EXAMPLE 29

6-(o-Cinnamidophenethyl)-N,N-diethyl-1-methylpiperidine-3-carboxamide mucate (Racemate A)

Reaction of the Racemate A of 6-(o-aminophenethyl)-N,N-diethyl-1-methylpiperidine-3-carboxamide (5.1 g., 0.16 mole) obtained in Example 4 (f) with cinnamoyl chloride (3.2 g., 0.19 mole) in 70 ml. of pyridine according to the method of Example 25 provides 7.3 g. of the free piperidine carboxamide base. The free base reacted with mucic acid in boiling methanol provides the mucate salt. This methanol soluble mucate salt is dissolved in methanol and precipitated therefrom by the addition of isopropyl ether. Crystallization from ethanol-isopropyl ether provides 3.4 g. of 6-(o-cinnamidophenethyl)-N,N-diethyl-1-methylpiperidine-3-carboxamide mucate hydrated with water, m.p. 79°-110° C.

Analysis. Calcd. for $C_{28}H_{37}N_3O_2.\frac{1}{2}C_6H_{10}O_8.\frac{1}{2}H_2O$: C, 64.45; H, 7.50; N, 7.27. Found: C, 64.38; H, 7.69; N, 6.89.

Crystallization of this material from methanol provides a methanol solvated mucate salt. The methanol solvate is removed by drying at 82° C. in vacuo for 24 hr. to provide a methanol free product having a melting point of 117°-120° C. (corr.).

EXAMPLE 30

6-(O-Cinnamidophenethyl)-N,N-diethyl-1-methylpiperidine-3-carboxamide cinnamate (Racemate B)

Reaction of the Racemate B of 6-(o-aminophenethyl)-N,N-diethyl-1-methylpiperidine-3-carboxamide (4.1 g., 0.13 mole) obtained in Example 4 (f) with cinnamoyl chloride (2.6 g., 0.015 mole) in 40 ml. of pyridine according to the method of Example 25 provides 6.0 g., of the free base. The free base is taken up in 100 ml. of ethanol and treated with cinnamic acid (1.98 g., 0.013 mole). The cinnamic acid salt of 6-(o-cinnamidophenethyl)-N,N-diethyl-1-methylpiperidine-3-carboxamide is precipitated from the ethanolic solution by the addition of isopropyl ether to provide 5.3 g. of solid with a melting point of 156°-160° C.

Crystallization from methanol-isopropyl ether provides analytically pure Racemate B product which has a melting point of 158°-164° C. (corr.).

Analysis. Calcd. for $C_{28}H_{37}N_3O_2.C_9H_8O_2$:C, 74.59; H, 7.61; N, 7.05. Found: C, 74.33; H, 7.89; N, 7.07.

EXAMPLE 31

2'-[2-(5-Ethyl-1-methyl-2-piperidyl)-ethyl]cinnamanilide hydrochloride (Racemate A)

Reaction of 2'-(o-aminophenethyl)-5-ethyl-1-methylpiperidine (3.3 g., 0.0134 mole) obtained in Example 5 (f) with cinnamoyl chloride (2.7 g., 0.016 mole) in 50 ml. of pyridine according to the method of Example 25 provides 4.2 g. of the hydrochloric salt, m.p. 184°-186° C. Crystallization of the salt from isopropanol affords 3.6 g., (65%) of 2'-[2-(5-ethyl-1-methyl-2-piperidyl)ethyl]cinnamaldehyde hydrochloride (Racemate A), m.p. 184°-187° C. (corr.).

Analysis. Calcd. for $C_{25}H_{33}ClN_2O$: C, 72.70; H, 8.05; N, 6.78. Found: C, 72.82; H, 8.37; N, 6.45.

EXAMPLE 32

2'-[2-(5-Ethyl-1-methyl-2-piperidyl)-ethyl]cinnamanilide hydrate (Racemate B)

Racemate B of 5-ethyl-2'-(o-formamidophenethyl)-1-methylpiperidine free base (5.5 g., 0.0224 mole) obtained in Example 5 (f) reacted with cinnamoyl chloride (4.1 g., 0.0246 mole) in 75 ml. of pyridine according to the method of Example 25 provides 2'-[2-(5-ethyl-1-methyl-2-piperidyl)ethyl]cinnamanilide (Racemate B). This substance is purified by crystallization from acetone containing a trace of water and yields 3.4 g of 2'-[2-(5-ethyl-1-methyl-2-piperidyl)ethyl]cinnamanilide hydrate, m.p. 91°-98° C. (corr.).

Analysis. Calcd. for $C_{25}H_{32}N_2O.H_2O$: C, 76.10; H, 8.69; N, 7.10; $H_2O$, 4.57. Found: C, 76.24; H, 8.47; N, 7.19; $H_2O$, 4.29.

EXAMPLES 33-54

Additional Cinnamanilides and formanilides

The cinnamanilides and formanilides listed in Table II are prepared from the specified reactants according to the procedures described in Examples 25-32 as will be clear to those skilled in the art.

TABLE II

ADDITIONAL CINNAMANILIDES AND FORMANILIDES

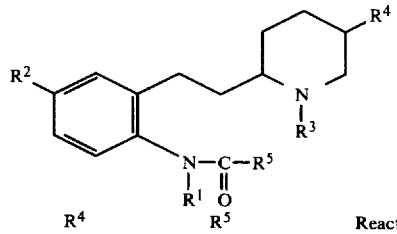

| Example | $R^1$ | $R^2$ | $R^3$ | $R^4$ | $R^5$ | Reactants |
|---|---|---|---|---|---|---|
| 33 | $C_2H_5$ | n-$C_4H_9$ | $CH_3$ | H | —CH=CH—ϕ | 2-(2-ethylamino-5-n-butoxyphenethyl)-1-methylpiperidine and cinnamoyl chloride |
| 34 | $C_2H_5$ | n-$C_4H_9O$ | $CH_3$ | H | H | 2-(2-ethylamino-5-n-butoxyphenethyl)-1-methylpiperidine and formic acid-acetic anhydride |
| 35 | $CH_3$ | H | n-$C_4H_9$ | H | —CH=CH—ϕ | 2-(o-methylaminophenethyl)-1-n-butylpiperidine and cinnamoyl chloride |
| 36 | $CH_3$ | H | $(CH_3)_2CH$ | H | H | 2-(o-methylaminophenethyl)-1-isopropylpiperidine and formic acid-acetic anhydride |
| 37 | n-$C_4H_9$ | H | $CH_3$ | H | —CH=CH—ϕ | 2-(2-n-butylaminophenethyl)-1-methylpiperidine and cinnamoyl chloride |
| 38 | n-$C_4H_9$ | H | $CH_3$ | H | H | 2-(2-n-butylaminophenethyl)-1-methylpiperidine and formic acid-acetic anhydride |
| 39 | H | H | $CH_3$ | $CH_3$ | —CH=CH—ϕ | 2-(o-aminophenethyl)-5-methyl-1-methylpiperidine and cinnamoyl chloride |
| 40 | H | H | $CH_3$ | $CH_3$ | H | 2-(o-aminophenethyl)-5-methyl-1-methylpiperidine and formic acid-acetic anhydride |
| 41 | H | H | $CH_3$ | n-$C_4H_9$ | —CH=CH—ϕ | 2-(o-aminophenethyl)-5-n-butyl-1-methylpiperidine and cinnamoyl chloride |
| 42 | H | H | $CH_3$ | n-$C_4H_9$ | H | 2-(o-aminophenethyl)-5-n-butyl-1-methylpiperidine and formic acid-acetic anhydride |
| 43 | H | $(CH_3)_2CHO$ | $CH_3$ | $(CH_3)_2CH$ | —CH=CH—ϕ | 2-(2-amino-5-isopropoxyphenethyl)-5-isopropyl-1-methylpiperidine and cinnamoyl chloride |
| 44 | H | $(CH_3)_2CHO$ | $CH_3$ | $(CH_3)_2CH$ | H | 2-(2-amino-5-isopropoxyphenethyl)-5-isopropyl-1-methylpiperidine and formic acid-acetic anhydride |
| 45 | H | H | $CH_3$ | $CON(CH_3)_2$ | —CH=CH—ϕ | 6-(o-aminophenethyl)-N,N-dimethyl-1-methylpiperidine-3-caboxamide and cinnamoyl chloride |
| 46 | H | H | $CH_3$ | $CON(CH_3)_2$ | H | 6-(o-aminophenethyl)-N,N-dimethyl-1-methylpiperidine-3-carboxamide and formic acid-acetic anhydride |
| 47 | H | H | $CH_3$ | $CON(n\text{-}C_4H_9)_2$ | —CH=CH—ϕ | 6-(o-aminophenethyl)-N,N-di-n-butyl-1-methylpiperidine-3-carboxamide and formic acid-acetic anhydride |
| 48 | H | H | $CH_3$ | $CON(n\text{-}C_4H_9)_2$ | H | 6-(o-aminophenethyl)-N,N-di-n-butyl-1-methylpiperidine-3-carboxamide and formic acid-acetic anhydride |
| 49 | $CH_3$ | $CH_3O$ | $CH_3$ | $CON(C_2H_5)_2$ | —CH=CH—ϕ | 6-(2-methylamino-5-methoxyphenethyl)-N,N-diethyl-1-methylpiperidine-3-carboxamide and cinnamoyl chloride |
| 50 | $CH_3$ | $CH_3O$ | $CH_3$ | $CON(C_2H_5)_2$ | H | 6-(2-methylamino-5-methoxyphenethyl)-N,N-diethyl-1-methylpiperidine-3-carboxamide and formic acid-acetic anhydride |
| 51 | H | H | $CH_3$ | H | —C(C₂H₅)=CH—ϕ | 2-(o-aminophenethyl)-1-methylpiperidine and α-ethylcinnamoyl chloride |

TABLE II-continued

ADDITIONAL CINNAMANILIDES AND FORMANILIDES

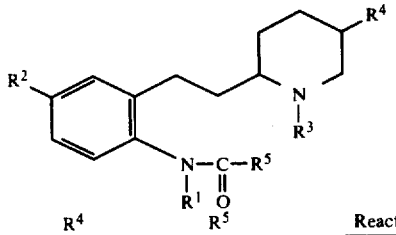

| Example | $R^1$ | $R^2$ | $R^3$ | $R^4$ | $R^5$ | Reactants |
|---|---|---|---|---|---|---|
| 52 | n-$C_4H_9$ | H | $CH_3$ | H | $-C(C_2H_5)=CH-\phi$ | 2-(2-n-butylaminophenethyl)-1-methylpiperidine and α-ethylcinnamoyl chloride |
| 53 | H | H | $CH_3$ | H | $-C(n\text{-}C_4H_9)=CH-\phi$ | 2-(o-aminophenethyl)-1-methylpiperidine and α-n-butylcinnamoyl chloride |
| 54 | H | H | $CH_3$ | H | $-C(CH(CH_3)_2)=CH-\phi$ | 2-(o-aminophenethyl)-1-methylpiperidine and α-isopropylcinnamoyl chloride |

EXAMPLE 55

'-[2-(1-Methyl-2-piperidyl)ethyl]-2-thiophenecarboxanilide mucate

2-Thiophencarbonyl chloride (11.7 g., 0.088 mole) is added in one portion to 2-(o-aminophenethyl)-1-methylpiperidine (10.0 g., 0.046 mole) in 50 ml. of pyridine with stirring. The mixture stirred for 0.5 hr. and concentrated in vacuo provides a residue which is taken up in 50 ml. of water and made basic (pH 9–10) with potassium carbonate. The aqueous mixture is extracted with ether, the ethereal extract washed with water and after drying over magnesium sulfate, concentrated to provide the thiophenecarboxanilide base.

The mucate salt is prepared by dissolving the free base in ethanol and adding mucic acid to the ethanolic solution until solid mucic acid no longer dissolves. Insoluble mucic acid is removed by filtration and the ethanolic filtrate diluted with ethyl acetate to incipient turbidity. This provides 14.0 g. of the mucate salt which crystallized from ethanol-ethyl acetate provides 6.4 g. of analytically pure 2'-[2-(1-methyl-2-piperidyl)-ethyl]-2-thiophenecarboxanilide, m.p. 143.5°–146° C. (corr.).

Analysis. Calcd. for $C_{19}H_{24}N_2OS.\frac{1}{2}C_6H_{10}O_8$: C, 60.95; H, 6.74; N, 6.46; S, 7.40. Found: C, 60.83; H, 6.57; N, 6.43; S, 7.22.

EXAMPLES 56–64

Additional Thiophenecarboxanilides

By substituting the appropriate 2-(o-aminophenethyl)piperidine in lieu of 2-(o-aminophentyl)-1-methylpiperidine in Example 55, the thiophenecarboxanilides of Table III are prepared.

TABLE III

ADDITIONAL THIOPHENECARBOXANILIDES

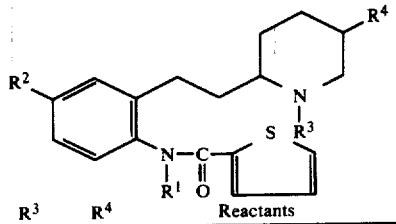

| Example | $R^1$ | $R^2$ | $R^3$ | $R^4$ | Reactants |
|---|---|---|---|---|---|
| 56 | $CH_3$ | H | $CH_3$ | H | 2-(o-methylaminophenethyl)-1-methylpiperidine and 2-thiophenecarbonyl chloride |
| 57 | n-$C_4H_9$ | H | $CH_3$ | H | 2-(2-n-butylaminophenethyl)-1-methylpiperidine and 2-thiophenecarbonyl chloride |
| 58 | H | $CH_3O$ | $CH_3$ | H | 2-(2-amino-5-methoxyphenethyl)-1-methylpiperidine and 2-thiophenecarbonyl chloride |
| 59 | H | n-$C_4H_9O$ | $CH_3$ | H | 2-(2-amino-5-n-butoxyphenethyl)-1-methylpiperidine and 2-thiophenecarbonyl chloride |
| 60 | H | H | n-$C_4H_9$ | H | 2-(o-aminophenethyl)-1-n-butylpiperidine and 2-thiophenecarbonyl chloride |
| 61 | H | H | $CH_3$ | $CH_3$ | 2-(o-aminophenethyl)-5-methyl-1-methylpiperidine and 2-thiophenecarbonyl chloride |
| 62 | H | H | $CH_3$ | n-$C_4H_9$ | 2-(o-aminophenethyl)-5-n-butyl-1-methylpiperidine and 2-thiophenecarbonyl chloride |
| 63 | H | $(CH_3)_2CHO$ | $CH_3$ | H | 2-(2-amino-5-isopropoxyphenethyl)-1-methylpiperidine and 2-thiophenecarbonyl chloride |
| 64 | H | H | $CH_3$ | $CON(C_2H_5)_2$ | 6-(o-aminophenethyl)-N,N-diethyl-1-methylpiperidine-3-carboxamide and 2-thiophenecarbonyl chloride |

EXAMPLE 65

2′-[2-(1-Methyl-2-piperidyl)ethyl]-acetanilide mucate.

By substituting a molar equivalent of acetyl chloride in lieu of cinnamoyl chloride in Example 25, 2′-[2-(1-methyl-2-piperidyl)ethyl]acetanilide free base is obtained. The crude free base is converted to the crystalline mucate according to the procedure of Example 26 and crystallized from ethanol to provide analytically pure 2′-[(2-(1-methyl-2-piperidyl)ethyl]acetanilide mucate, m.p. 173.5°-174.5° C. (corr.).

Analysis. Calcd. for $C_{16}H_{24}N_2O.\frac{1}{2}C_6H_{10}O_8$: C, 62.44; H, 8.00; N, 7.66. Found: C, 62.47; H, 8.29; N, 7.79.

An alternative preparation of 2′-[2-(1-methyl-2-piperidyl)ethyl]acetanilide mucate is as follows. 2-(o-Acetamidophenethyl)pyridine (12.6 g., 0.05 mole) obtained according to D. H. Hey and J. M. Osbond, J. Chem. Soc., 3170 (1949), is reacted with methyl iodide (7.9 g., 0.055 mole) in 100 ml. of acetone according to the method of Example 2 (c) to provide 11.5 g. (60%) of 2-(o-acetamidophenetyl)pyridinium iodide, m.p. 229.5°-231.5° C. (corr.), (crystallized from ethanol).

Analysis. Calcd. for $C_{16}H_{19}IN_2O$: C, 50.37; H, 5.01; N, 7.33. Found: C, 49.97; H, 4.84; N, 7.22.

Reduction of 2-(o-acetamidophenethyl)pyridinium iodide in ethanol employing platinum oxide catalyst according to the procedure of Example 1 provides the piperidyl free base which is then converted to 2′-[2-(1-methyl-2-piperidyl)ethyl]acetanilide mucate according to Example 26.

EXAMPLE 66

6-(o-Acetamidophenethyl)-N,N-diethyl-1-methylpiperidine-3-carboxamide (Racemate A and Racemate B)

Acylation of 6-(o-aminophenethyl)-N,N-diethylnicotinamide in chloroform with acetic anhydride provides 6-(o-acetamidophenethyl)-N,N-diethylnicotinamide which methylated with methyl iodide in acetone according to the procedure of Example 2 (c) yields 2-(o-acetamidophenethyl)-5-diethylcarbamyl-1-methylpyridinium iodide. Passing an aqueous solution of 2-(o-acetamidophenethyl)-5-diethylcarbamyl-1-methylpyridinium idodide through a Dowex 21-K 50-100 mesh ion exchange column in the Cl— form provides 2-(o-acetamidophenethyl)-5-diethylcarbamyl-1-methylpyridinium chloride which is isolated by concentration of the aqueous solution.

Reduction of 2-(o-acetamidophenethyl)-5-diethylcarbamyl-1-methylpyridinium chloride in ethanol according to the method of Example 1 provides a mixture of the two racemates (Racemate A and Racemate B) of 6-(o-acetamidophenethyl)-N,N-diethyl-1-methylpiperidine-3-carboxamide which are chromatographically separated as follows. A chromatographic column (4 cm. diameter) is packed to a height of 45 cm. with silica gel (300 g., 100-200 mesh, Davison Chemical Company, Grade 923) as a slurry in benzene. A mixture of Racemate A and B of 6-(o-acetamidophenethyl)-N,N-diethyl-1-methylpiperidine-3-carboxamide (10.8 g.) is loaded on the column in 50 ml. of benzene. The following 100 ml. fractions were collected. Fractions 1 to 3, benzene; fractions 4-43, ethanol-ethyl acetate 3:7+0.2% 58% $NH_4OH$; fractions 44-70, ethanolethyl acetate 1:1+0.5% 58 % $NH_4OH$; fractions 71∝84, ethanol +0.5% 58% $NH_4OH$. Fractions 5-36 are combined and evaporated to provide 2.4 g. of chromatographhically pure (thin-layer) Racemate A. Fractions 55-84 are combined and evaporated to provide 5.9 g. of Racemate B. Racemates A and B are further purified by distillation in a sublimator at 0.02 mm. Hg.

Analytical values, infrared and n.m.r. spectra are consistent for Racemate A and Racemate B.

Analysis. Calcd. for $C_{21}H_{33}N_3O_2$: C, 70.16; H, 9.26; N, 11.69. Found: (Racemate A) C, 70.51; H, 9.40; N, 11.82; (Racemate B) C, 70.03; H, 9.44; N, 11.75.

An alternate method of preparing Racemate A and Racemate B of 6-(o-acetamidophenethyl)-N,N-diethyl-1-methylpiperidine-3-carboxamide comprises the reaction of acetic anhydride with 6-(o-aminophenethyl)-N,N-diethyl-1-methylpiperidine-3-carboxamide Racemate A and Racemate B obtained in Example 4 (f).

EXAMPLES 67-75

Additional alkanoxyl anilides

The alkanoyl anilides listed in Table IV are prepared from the specified reactants according to the procedures of examples 25-32 as will be clear to those skilled in the art.

TABLE IV

ADDITIONAL ALKANOYL ANILIDES

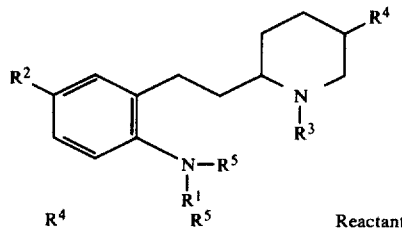

| Example | $R^1$ | $R^2$ | $R^3$ | $R^4$ | $R^5$ | Reactants |
|---|---|---|---|---|---|---|
| 67 | $CH_3$ | H | $CH_3$ | H | $CH_3CO$ | 2-(o-methylaminophenethyl)-1-methylpiperidine and acetic anhydride |
| 68 | n-$C_4H_9$ | H | $CH_3$ | H | $CH_3CO$ | 2-(2-n-butylaminophenethyl)-1-methylpiperidine and acetic anhydride |
| 69 | H | $CH_3O$ | $CH_3$ | H | $CH_3CO$ | 2-(2-amino-5-methoxyphenethyl)-1-methylpiperidine and acetic anhydride |
| 70 | H | H | n-$C_4H_9$ | H | $CH_3CO$ | 2-(o-aminophenethyl)-1-n-butylpiperidine and acetic anhydride |
| 71 | H | H | $CH_3$ | $C_2H_5$ | $CH_3CO$ | 2-(o-aminophenethyl)-5-ethyl-1-methylpiperidine and acetic anhydride |
| 72 | H | H | $CH_3$ | $CON(C_2H_5)_2$ | $CH_3CO$ | 6-(o-aminophenethyl)-N,N-diethyl-1-methylpiperidine-3-carboxamide and acetic anhydride |
| 73 | H | H | $CH_3$ | H | $CH_3(CH_2)_2CO$ | 2-(o-aminophenethyl)-1-methylpiperidine and |

TABLE IV-continued

ADDITIONAL ALKANOYL ANILIDES

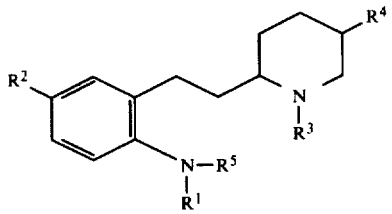

| Example | $R^1$ | $R^2$ | $R^3$ | $R^4$ | $R^5$ | Reactants |
|---|---|---|---|---|---|---|
| | | | | | | n-butyric anhydride |
| 74 | H | H | $CH_3$ | H | $(CH_3)_2CHCO$ | 2-(o-aminophenethyl)-1-methylpiperidine and iso-butyric anhydride |
| 75 | H | n-$C_4H_9O$ | $CH_3$ | H | $CH_3CH_2CO$ | 2-(2-amino-5-n-butoxyphenethyl)-1-methyl-piperidine and propionic anhydride |

Reduction of alkanoyl anilides with lithium aluminum hydrides provides 2-(o-alkylaminophenethyl)-1-alkylpiperidine intermediates which can be acylated or sulfonylated to provide additional products of the present invention. For example, reduction of alkanoyl anilides of Table IV wherein $R^1$ is hydrogen according to the method of Example 2 (e) with lithium aluminum hydride provides 2-(2-ethylamino-5-methoxyphenethyl)-1-methylpiperidine,
2-(o-ethylaminophenethyl)-1-n-butylpiperidine,
2-(o-ethylaminophenethyl)-5-ethyl-1-methylpiperidine,
2-(2n-butylaminophenethyl)-1-methylpiperidine,
2-(o-isobutylaminophenethyl)-1-methylpiperidine,
2-(2-n-propylamino-5-n-butoxyphenethyl)-1-methyl-piperidine.

EXAMPLE 76

2'-[2-(1-Methyl-2-piperidyl)ethyl]-methanesulfonanilide

Reaction of methanesulfonyl chloride (5.7 g., 0.05 mole) with 2-(o-aminophenethyl)-1-methylpiperidine (9.8 g., 0.045 mole) in 75 ml. of pyridine according to the procedure of Example 25 provides 5.6 g. (41%) of analytically pure 2'-[2-(1-methyl-2-piperidyl)ethyl]methanesulfonanilide (crystallized from ethanol), m.p. 91.5°-93.5° C. (corr.).

Analysis. Calcd. for $C_{15}H_{24}N_2O_2S$: C, 60.78; H, 8.16; N, 9.45. Found: C, 60.55; H, 8.12; N, 9.54.

EXAMPLES 77-86

Additional alkanesulfonanilides

The alkanesulfonanilides listed in Table V are prepared from the specified reactants according to the procedures of Examples 25-32 as will be clear to those skilled in the art.

TABLE V

ADDITIONAL ALKANESULFONANILIDES

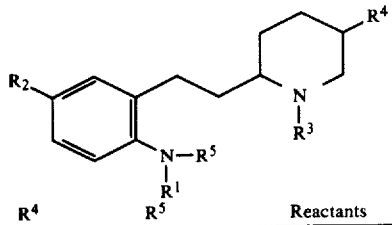

| Example | $R^1$ | $R^2$ | $R^3$ | $R^4$ | $R^5$ | Reactants |
|---|---|---|---|---|---|---|
| 77 | $CH_3$ | H | $CH_3$ | H | $CH_3SO_2$ | 2-(o-methylaminophenethyl)-1-methylpiperidine and methanesulfonyl chloride |
| 78 | n-$C_4H_9$ | H | $CH_3$ | H | $CH_3SO_2$ | 2-(2-n-butylaminophenethyl)-1-methylpiperidine and methanesulfonyl chloride |
| 79 | H | $CH_3O$ | $CH_3$ | H | $CH_3SO_2$ | 2-(2-amino-5-methoxyphenethyl)-1-methyl-piperidine and methansulfonyl chloride |
| 80 | H | H | n-$C_4H_9$ | H | $CH_3SO_2$ | 2-(o-aminophenethyl-1-n-butylpiperidine and methanesulfonyl chloride |
| 81 | H | H | $CH_3$ | $CH_3$ | $CH_3SO_2$ | 2-(o-aminophenethyl)-5-methyl-1-methyl-piperidine and methanesulfonyl chloride |
| 82 | H | H | $CH_3$ | $C_2H_5$ | $CH_3SO_2$ | 2-(o-aminophenethyl)-5-ethyl-1-methyl-piperidine and methanesulfonyl chloride |
| 83 | H | H | $CH_3$ | H | $CH_3(CH_2)_2SO_2$ | 2-(o-aminophenethyl)-1-methylpiperidine and n-butanesulfonyl chloride |
| 84 | H | H | $CH_3$ | H | $(CH_3)_2CHSO_2$ | 2-(o-aminophenethyl)-1-methylpiperidine and isopropanesulfonyl chloride |
| 85 | H | n-$C_4H_9O$ | $CH_3$ | H | $CH_3(CH_2)_2SO_2$ | 2-(2-amino-5-n-butoxyphenethyl)-1-methyl-piperidine and n-propanesulfonyl chloride |
| 86 | H | H | $CH_3$ | $CON(C_2H_5)_2$ | $CH_3SO_2$ | 6-(o-aminophenethyl)-N,N-diethyl-1-methyl-piperidine-3-carboxamide and methane-sulfonyl chloride |

EXAMPLE 87

4-Amino-2'-[2-(1-methyl-2-piperidyl)ethyl]benzanilide

Reaction of 4-nitrobenzoyl chloride (6.5 g., 0.035 mole) and 2-(o-aminophenethyl)-1-methylpiperidine (6.0 g., 0.0275 mole) in 35 ml. of pyridine according to the method of Example 25 provides 2'-[2-(1-methyl-2-piperidyl)ethyl]-4-nitrobenzanilide. Crystallization from ethyl acetate provides analytically pure material, m.p. 162°-163.5° C.

Analysis. Calcd. for $C_{21}H_{25}N_3O_3$: C, 68.64; H, 6.86; N, 11.44. Found: C, 68.58; H, 6.84; N, 11.30.

Reduction of 2'-[2-(1-methyl-2-piperidyl)ethyl]-4-nitrobenzanilide (6.5 g., 0.018 mole) in 100 ml. of ethanol employing 2 g. of palladium on carbon catalyst (10%) according to Example 2 (a) affords 4-amino-2'-[2-(1-methyl-2-piperidyl)-ethyl]benzanilide. Crystallization of the product from acetonitrile provides the analytically pure substance, m.p. 147°-148.5° C. (corr.).

Analysis. Calcd. for $C_{21}H_{27}N_3O$: C, 74.74; H, 8.07; N, 12.45. Found: C, 74.75; H, 8.06; N, 12.47.

EXAMPLE 88

4-Acetoxy-2'-[2-(1-methyl-2-piperidyl)ethyl]benzanilide

Reaction of 2-(o-aminophenethyl)-1-methylpiperidine with p-acetoxybenzoyl chloride in pyridine according to Example 1 provides 4-acetoxy-2'-[2-(1-methyl-2-piperidyl)-ethyl]benzanilide. Analytically pure product is obtained by crystallization from isopropyl ether, m.p. 88°-108° C. (corr.). The broad melting point of the analytically pure material is due to polymorphism.

Analysis. Calcd. for $C_{23}H_{28}N_2O_3$: C, 72.60; H, 7.42; N, 7.36. Found: C, 72.79; H, 7.38; N, 7.31.

EXAMPLE 89

4-Hydroxy-2'-[2-(1-methyl-2-piperidyl)ethyl]benzanilide

4'-Acetoxy-2'-[2-(1-methyl-2-piperidyl)-ethyl]benzanilide suspended in 1 N sodium hydroxide is stirred until solution takes place. The pH of the aqueous solution is adjusted to 9 with 6 N hydrochloric acid and an oil precipitates which is extracted with ethyl acetate. The product isolated by removal of the ethyl acetate solvent is crystallized from ethanol to provide analytically pure 4-hydroxy-2'-[2-(1-methyl-2-piperidyl)ethyl]-benzanilide, m.p. 178.5°-182.5° C. (corr.).

Analysis. Calcd. for $C_{21}H_{26}N_2O_2$: C, 74.52; H, 7.74; N, 8.28. Found: C, 74.59; H, 7.47; N, 8.31.

EXAMPLES 90-111

Additional Benzanilides

The benzanilides listed in Table VI and Table VII are prepared according to the procedures of Examples 25-32 and 87-89 as will be clear to those skilled in the art.

TABLE VI

ADDITIONAL BENZANILIDES

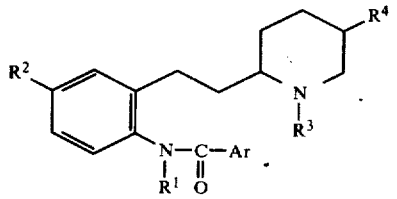

| Example | $R^1$ | $R^2$ | $R^3$ | $R^4$ | Ar | Reactants |
|---|---|---|---|---|---|---|
| 90 | $CH_3$ | H | $CH_3$ | H | $C_6H_5$ | 2-(o-methylaminophenethyl)-1-methylpiperidine and benzoyl chloride |
| 91 | n-$C_4H_9$ | H | $CH_3$ | H | $C_6H_5$ | 2-(2-n-butylaminophenethyl)-1-methylpiperidine and benzoyl chloride |
| 92 | H | $CH_3O$ | $CH_3$ | H | $C_6H_5$ | 2-(2-amino-5-methoxyphenethyl)-1-methylpiperidine and benzoyl chloride |
| 93 | H | n-$C_4H_9O$ | $CH_3$ | H | $C_6H_5$ | 2-(2-amino-5-n-butoxyphenethyl)-1-methylpiperidine and benzoyl chloride |
| 94 | H | H | n-$C_4H_9$ | H | $C_6H_5$ | 2-(o-aminophenethyl)-1-n-butylpiperidine and benzoyl chloride |
| 95 | H | H | $CH_3$ | $CH_3$ | $C_6H_5$ | 2-(o-aminophenethyl)-5-methyl-1-methylpiperidine and benzoyl chloride |
| 96 | H | H | $CH_3$ | n-$C_4H_9$ | $C_6H_5$ | 2-(o-aminophenethyl-5-n-butyl-1-methylpiperidine and benzoyl chloride |
| 97 | H | H | $CH_3$ | H | p-n-$C_4H_9$—S—$C_6H_5$ | 2-(o-aminophenethyl)-1-methylpiperidine and p-n-butylthiobenzoyl chloride |
| 98 | H | H | $CH_3$ | H | m-$C_4H_9$—O—$C_6H_4$ | 2-(o-aminophenethyl)-1-methylpiperidine and m-n-butoxybenzoyl chloride |
| 99 | H | H | $CH_3$ | H | 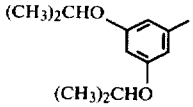 | 2-(o-aminophenethyl)-1-methylpiperidine and 3,5-diisopropoxybenzoyl chloride |
| 100 | H | H | $CH_3$ | H | 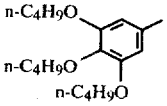 | 2-(o-aminophenethyl)-1-methylpiperidine and 3,4,5-tri-n-butoxybenzoyl chloride |
| 101 | H | H | $CH_3$ | H | p-F—$C_6H_4$ | 2-(o-aminophenethyl)-1-methylpiperidine and 4-fluorobenzoyl chloride |
| 102 | H | H | $CH_3$ | $CON(C_2H_5)_2$ | $C_6H_5$ | 6-(o-aminophenethyl)-N,N-diethyl-1-methylpiperidine-3-carboxamide and |

TABLE VI-continued

ADDITIONAL BENZANILIDES

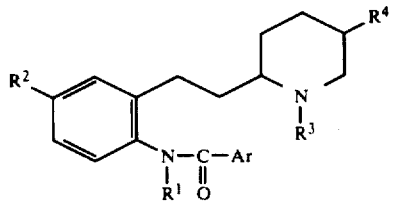

| Example | $R^1$ | $R^2$ | $R^3$ | $R^4$ | Ar | Reactants |
|---|---|---|---|---|---|---|
| 103 | H | $CH_3O$ | $CH_3$ | H | p-$NH_2C_6H_4$ | benzoyl chloride 2-(2-amino-5-methoxyphenethyl)-1-methylpiperidine and p-nitrobenzoyl chloride |

TABLE VII

ADDITIONAL BENZANILIDES

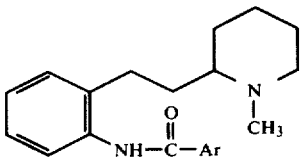

| Example | Chemical Name | Ar | M.P. °C. | Analysis Calcd. | Analysis Found |
|---|---|---|---|---|---|
| 104 | 2'-[2-(1-methyl-1-piperidyl)ethyl]-benzanilide | 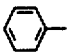 | 85.5–87 | C 78.22 H 8.13 N 8.69 | C 78.41 H 8.13 N 8.68 |
| 105 | 4-chloro-2'-[2-(1-methyl-2-piperidyl)-ethyl]benzanilde | 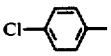 | 130–131 | C 70.67 H 7.06 N 7.85 | C 70.84 H 7.05 N 7.84 |
| 106 | 4-(methylthio)-2'-[2-(1-methyl-2-piperidyl)ethyl]benzanilide | 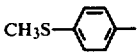 | 145–145.5 | C 71.70 H 7.66 N 7.60 | C 71.86 H 7.59 N 7.54 |
| 107 | 4-methoxy-2'-[2-(1-methyl-2-piperidyl)ethyl]benzanilide | 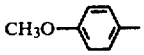 | 131.5–132.5 | C 74.96 H 8.01 N 7.95 | C 74.91 H 7.83 N 7.90 |
| 108 | 3-methoxy-2'-[2-(1-methyl-2-piperidyl)ethyl]benzanilide | 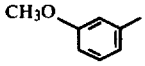 | 124.5–126.5 | C 74.96 H 8.01 N 7.95 | C 75.16 H 7.94 N 7.88 |
| 109 | 3,4-dimethoxy-2'-[2-(1-methyl-2-piperidyl)ethyl]benzanilide | 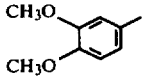 | 123–124.5 | C 72.22 H 7.91 N 7.32 | C 72.12 H 7.88 N 7.39 |
| 110 | 3,5-dimethoxy-2'-[2-(1-methyl-2-piperidyl)ethyl]benzanilide hydrogen maleate | 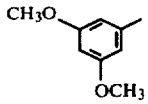 | 140.5–142 | C 65.04 H 6.87 N 5.62 | C 65.00 H 6.93 N 5.65 |
| 111 | 2'-[2-(1-methyl-2-piperidyl)-ethyl]3,4,5-trimethoxy-benzanilide mucate hydrate | 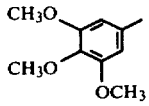 | 115–122 | C 60.54 H 7.34 N 5.23 | C 60.33 H 7.21 N 5.18 |

EXAMPLE 112

Pharmaceutical Compositions

The substituted piperidines characterized by Formula I are compounded with pharmacologically acceptable carriers to provide compositions useful in the present invention. Typical of the pharmaceutical compositions are the following:

A. Tablets. The piperidines of Formula I are compounded into tablets according to the following example.

| Material | Amount |
|---|---|
| 4-Methoxy-2'-[2-(1-methyl-2-piperidyl)-ethyl]benzanilide | 50.0 g. |
| Magnesium stearate | 1.3 g. |
| Corn starch | 12.4 g. |
| Corn starch pregelatinized | 1.3 g. |
| Lactose | 185.0 g. |

The foregoing materials are blended in a twin-shell blender and then granulated and pressed into tablets weighing 250 mg. each. Each tablet contains 50 milligrams of active ingredient. The tablet may be scored in quarters so that a dose of 12.5 mg. of active ingredient may be conveniently obtained.

B. Capsules. The piperidines of Formula I are compounded into capsules according to the following example.

| Materials | Amount |
|---|---|
| Active Ingredient | 125 mg. |
| Lactose | 146.0 mg. |
| Magnesium stearate | 4.0 mg. |

The foregoing materials are blended in a twin-shell blender and then filled into No. 1 hard gelatin capsules. Each capsule contains 125 mg. of active ingredient.

C. Solution of Intravenous Administration

The substituted piperidines characterized by Formula I are formulated for parenteral administration according to the following example. A sterile solution suitable for intravenous injection is prepared by dissolving 10.0 g. of 4-methoxy-2'-[2-(1-methyl-2-piperidyl)ethyl]benzanilide in a minimal amount of 0.5 N hydrochloric acid. This solution is adjusted to a pH of 4.3 with 0.1 N sodium hydroxide and diluted to 1000 ml. total volume with saline. The solution is sterilized by passage through a bacteriological filter and aseptically filled into 10 ml. sterile ampoules. Each milliliter of solution contains 10 mg. of the active ingredient, 4-methoxy-2'-[2-(1-methyl-2-piperidyl)ethyl]benzanilide.

EXAMPLE 113

4-(t-Butoxy)-2'-[2-(1-methyl-2-piperidyl)methyl]benzanilide

A mixture of 2-(o-aminophenethyl)piperidine (38.8 g., 0.178 mole), methyl-4-(t-butoxy)benzoate (36.9 g., 0.178 mole), sodium methoxide (10.6 g., 0.195 mole) and 600 ml. of benzene is heated to reflux in a flask fitted with a 30 cm vacuum-jacketed fractionating column packed with Rashig rings, and a variable takeoff head. The methanol-benzene azeotrope is removed at intervals until no more forms. After cooling to 25° C., the mixture is washed ($H_2O$, sat. brine) dried ($MgSO_4$), and evaporated. Crystallization of the residue thus obtained from heptane yields 15.2 g. (21%) of 4-(t-butoxy)-2'-[2-(1-methyl-2-piperidyl)ethyl]benzanilide, m.p. 91°-93.5° C. (corr.).

Analysis. Calcd. for $C_{25}H_{34}N_2O_2$: C, 76.10; H, 8.69; N, 7.10. Found: C, 76.06; H, 8.59; N, 7.10.

EXAMPLE 114

2'-[2-(1-Methyl-2-piperidyl)ethyl]-p-toluanilide

Reaction of 2-(o-aminophenethyl)-1-methylpiperidine (80 g., 0.036 mole) with p-toluoyl chloride (6.2 g., 0.04 mole) in 50 ml. of pyridine according to the method of Example 25 provides 2'-[2-(1-methyl-2-piperidyl)ethyl]p-toluanilide. Crystallization from isopropyl ether and then from isopropyl alcohol provides 3.9 g., (32%) of analytically pure material, m.p. 90.5°-92° C. (corr.).

Analysis. Calcd. for $C_{22}H_{28}N_2O$: C, 78.53; H, 8.39; N, 8.33. Found: C, 78.56; H, 8.09; N, 8.05.

EXAMPLE 115

2'-[2-(1-Methyl-2-piperidyl)ethyl]picolinanilide

A solution of 2-(o-aminophenethyl)-1-methylpiperidine (8.0 g., 0.037 mole) and ethyl picolinate (5.5 g., 0.037 mole) in DMSO (20 ml.) is treated with NaH (57%) in oil (1.6 g., 0.037 mole) with intermittent cooling to moderate the resulting vigorous reaction. After 2 hr., the mixture is poured into 150 ml. of $H_2O$ and the product isolated according to the procedure of Example 25. Crystallization from isopropyl ether affords 5.9 (50%) of analytically pure 2'-[2-(1-methyl-2-piperidyl)ethyl]picolinanilide, m.p. 65.5°-67° C. (corr.).

Analysis. Calcd. for $C_{20}H_{25}N_3O$: C, 74.27; H, 7.79; N, 12.99. Found: C, 74.33; H, 7.92; N, 12.99.

EXAMPLE 116

2-[2-[2-(1-Methyl-2-piperidyl)ethyl]phenylcarbamoyl]-benzoic acid

To a solution of 2-(o-aminophenethyl)-1-methylpiperidine (8.73 g., 0.04 mole) in 100 ml. of EtOAc is rapidly added a solution of phthalic anhydride (5.93 g., 0.04 mole) in 100 ml. of EtOAc. Solid product separates after a short time and is collected and crystallized from $CH_3CN$, yielding 7.2 g. (49%) of 2-[2-[2-(1-methyl-2-piperidyl)ethyl]phenylcarbamoyl]benzoic acid, m.p. 171°-172° C. (corr.).

Analysis. Calcd. for $C_{22}H_{26}N_2O_3$: C, 72.10; H, 7.15; N, 7.65. Found: C, 72.22; H, 7.10; N, 7.81.

EXAMPLE 117

2'-[2-(1-Methyl-2-piperidyl)ethyl]isonipecoticanilide

2'-[2-(1-Methyl-2-piperidyl)ethyl]isonicotinanilide hydrate (9.7 g., 0.028 mole) is hydrogenated on a Parr apparatus in glacial acetic acid (200 ml.) using 10% Pd/C (4.0 g.) as the catalyst. Evaporation of the AcOH followed by a basic workup according to the procedure of Example 25 affords the crude product which crystallized from EtOAc yields 4.3 g. (46%) of 2'-[2-(1-methyl-2-piperidyl)ethyl]isonipecoticanilide, m.p. 157°-159° C. (corr.).

Analysis. Calcd. for $C_{20}H_{31}N_3O$: C, 72.90; H, 9.48; N, 12.76. Found: C, 73.30; H, 9.46; N, 12.76.

EXAMPLE 118

4-Methoxy-2'-[2-(1-methyl-2-piperidyl)propyl]benzanilide a. 2-(β-Methyl-2-nitrostyryl)pyridine A mixture of o-nitrobenzaldehyde (127 g., 0.84 mole), 2-ethylpyridine (90 g., 0.84 mole) and acetic anhydride (171 g., 1.68 mole) is heated at reflux for 24 hr. Excess acetic anhydride is evaporated in vacuo and the residue poured into 500 ml. of water. The mixture is adjusted to pH 11 with 50% NaOH providing a precipitate which is collected and dried. Crystallization from isopropyl ether yields 136.7 g. (67%) of 2-β-methyl-2-nitrostyryl)-pyridine, m.p. 62°-64° C. which, after a second crystallization, is analytically pure.

Analysis. Calcd. for $C_{14}H_{12}N_2O_2$: C, 69.99; H, 5.03; N, 11.66. Found: C, 70.38; H, 5.07; N, 11.70.

b. 2-[2-(2-Aminophenyl)-1-methylethyl]pyridine 2-(β-Methyl-2-nitrostyryl)pyridine (24.0 g., 0.1 mole) is hydrogenated on a Parr apparatus in 200 ml. of ethanol with 3 g. of 10% Pd/C as catalyst. The catalyst is filtered and the filtrate evaporated, providing 2-[2-(2-aminophenyl)-1-methylethyl]pyridine.

c. 2-[2-(2-Formamidophenyl)-1-methylethyl]pyridine

Reaction of 2-[2-(2-aminophenyl)-1-methylethyl]-pyridine (21 g., 0.1 mole) with 42 ml. of acetic-formic anhydride, according to the procedure of Example 2(b), affords 2-[2-(2-formamidophenyl)-1-methylethyl]-1-methylpyridinium iodide.

d. 2-[2-(2-Formamidophenyl)-1-methylethyl]-1-methylpyridinium iodide

Reaction of 2-[2-(2-formamidophenyl)-1-methylethyl]pyridine (24 g., 0.1 mole) with methyl iodide (28.4 g., 0.2 mole) according to the procedure of Example 2(c), affords 29.5 g. (77%) of 2-[2-(2-formamidophenyl)-1-methylethyl]-1-methylpyridinium iodide, m.p. 184°-188° C.

Analysis Calcd. for $C_{16}H_{19}IN_2O$: C, 50.28; H, 5.01; N, 7.33. Found: C, 50.46; H, 5.01; N, 7.20.

e. 2-[2-(2-Aminophenyl)-1-methylethyl]-1-methylpiperidine

2-[2-(2-Formamidophenyl)-1-methylethyl]-1-methylpyridinium iodide (25.4 g., 0.0665 mole) is hydrogenated in a Parr apparatus in 200 ml. of ethanol with $Pt_2O$ (0.6 g.) as catalyst. A basic workup gave 2-[2-(2-formamidophenethyl)-1-methylethyl]-1-methylpiperidine which is dissolved in 200 ml. of methanol, mixed with 45 ml. of concentrated hydrochloric acid, permitted to stand for 24 hr. and then heated at reflux for 4 hr. A basic workup and distillation yields 2-[2-(2-aminophenyl)-1-methylethyl]-1-methylpiperidine, $n_D^{25°}$, 1.5520, b.p. 121°-124° C./0.1 Torr.

Analysis Calcd. for $C_{15}H_{24}N_2$: C, 77.53; H, 10.41; N, 12.06. Found: C, 77.26; H, 10.46; N, 12.07.

f. 4-Methoxy-2'-[2-methyl-2-(1-methyl-2-piperidyl)ethyl]benzanilide

Reaction of 2-[2-(2-aminophenyl)-1-methylethyl]-1-methylpiperidine with anisoyl chloride, according to the procedure of Example 25, provides 4-methoxy-2'-[2-methyl-2-(1-methyl-2-piperidyl)ethyl]benzanilide as a 72:28 mixture of diastereoisomers (according to nmr), m.p. 125.5°-136.5° C. (corr.).

Analysis. Calcd. for $C_{23}H_{30}N_2O_2$: C, 75.37; H, 8.25; N, 7.64. Found: C, 75.24; H, 8.42; N, 7.34. The diastereoisomeric mixture of 4-methoxy-2'-[2-methyl-2-(1-methyl-2-piperidyl)ethyl]benzanilide (42 g.) is fractionally recrystallized from ethyl acetate following a triangular scheme according to the technique of A. Weissberger and E. S. Proshauer, "Technique of Organic Chemistry" Vol. III, 490, Interscience Publishers, Inc., New York, 1955 as follows:

| Crop | Wt. g. | M.P.(°C.) | A:B Ratio of Racemates by nmr |
|---|---|---|---|
| 1 | 15.3 | 117-121 | — |
| 1A | 11.4 | 123-135 | 72:28 |
| 1B | 4.9 | 136-143 | — |
| 1C | 2.9 | 143-146 | 95:5 |
| 2 | 27.1 | 106-116 | — |
| 2A | 4.65 | 116-120 | 52:48 |
| 2B | 3.0 | 121-124 | 58:42 |
| 2C | 2.35 | 139-142 | 80:20 |
| 3 | 9.35 | 105-111 | 24:76 |
| 4 | 6.65 | 100-110 | 20:80 |

Crops 1C and 2C are combined and recrystallized to give 3.5 g. of Racemate A, 4-methoxy-2'-[2-methyl-2-(1-methyl-2-piperidyl)ethyl]benzanilide isomer (less than 5% Racemate B isomer), m.p. 146°-147.5° C. (corr.), δ, 2.1 (S, N—$CH_3$, 3H).

Crop 4 is recrystallized from isopropyl ether to provide 3.45 g. of Racemate B, 4-methoxy-2'-[2-methyl-2-(1-methyl-2-piperidyl)ethyl]benzanilide isomer (less than 5% Racemate A isomer), m.p. 96.0°-97.5° C. (corr.), δ, 2.25 (S, N—$CH_3$, 3H).

Analysis. Calcd. for $C_{23}H_{30}N_2O_2$: C, 75.37; H, 8.25; N, 7.64. Found: (Racemate A) C, 75.26; H, 8.24; N, 7.50; (Racemate B) C, 75.06; H, 8.32; N, 7.50.

EXAMPLE 119

2'-[2-(1-Ethyl-2-piperidyl)ethyl]-p-anisanilide a. 1-Ethyl-2-(o-formamidophenethyl)pyridinium iodide A solution of 2-(o-formamidophenethyl)pyridine (36.1 g., 0.159 mole) and iodoethane (30.0 g., 0.191 mole) in $Ch_3CN$ (450 ml.) heated at reflux for 18 hr., cooled and diluted to incipient turbidity provides 1-ethyl-2-(o-formamidophenethyl)pyridinium iodide, yield, 44.8 g. (74%), m.p. 155°-157° C.

b. 1-Ethyl-2-(2-formamidophenethyl)piperidine

To a solution of 1-ethyl-2-(o-formamidophenethyl)-pyridinium iodide (44.8 g., 0.117 mole), 50% NaOH (11.2 g., 0.14 mole), and water (40 ml.) in methanol (330 ml.) is added portionwise $NaBH_4$ (5.32 g., 0.14 mole). The solution is stirred for 2 hr. and evaporated. Water is added to the residue thus obtained and the mixture extracted with ether. The ethereal extracts are dried ($MgSO_4$) and evaporated. The residue taken up in 200 ml. of ethanol and hydrogenated in a Parr apparatus using 5 g. of 10% palladium on carbon as catalyst affords 1-ethyl-2-(2-formamidophenethyl)piperidine.

c. 2-(2-Aminophenethyl)-1-ethylpiperidine

A solution of 1-ethyl-2-(2-formamidophenethyl)-piperidine (27.6 g., 0.11 mole), methanol (450 ml.) and concentrated HCl (100 ml.) allowed to stand for 24 hr. provides 2-(2-aminophenethyl)-1-ethylpiperidine, purified by distillation, yield 17.72 g. (69%), b.p. 107°-128° C./0.1 Torr, $n_D^{30°}$ 1.5510.

Analysis. Calcd. for $C_{15}H_{24}N_2$: C, 77.53; H, 10.41; N, 12.06. Found: C, 77.29; H, 10.54; N, 11.87.

d. 2'-[2-(1-Ethyl-2-piperidyl)ethyl]-p-anisanilide

Reaction of 2-(2-aminophenethyl)-1-ethylpiperidine with anisoyl chloride according to the procudure of Example 25 provides 2'-[2-(1-ethyl-2-piperidyl)ethyl]-p-anisanilide, m.p. 136.5°-137.5° C. (corr.), from ethyl acetate.

Analysis. Calcd. for $C_{23}H_{30}N_2O_2$: C, 75.37; H, 8.25; N, 7.64. Found: C, 75.25; H, 8.30; N, 7.45.

EXAMPLE 120

4-Bromo-2'-[2-(1-Methyl-2-piperidyl)ethyl]-benzanilide

Reaction of 4-bromobenzoyl chloride with 2-(o-aminophenethyl)-1-methylpiperidine according to the procedure of Example 114 affords 4-bromo-2'-[2-(1-methyl-2-piperidyl)ethyl]benzanilide, m.p. 137.5°-138.5° C. (corr.), from ethyl acetate.

Analysis. Calcd. for $C_{21}H_{25}BrN_2O$: C, 62,83; H, 6.28; N, 6.98. Found: C, 62.55; H, 6.27; N, 6.92.

EXAMPLE 121

4-Fluoro-2'-[2-(1-methyl-2-piperidyl)ethyl]-benzanilide

Reaction of 2-(o-aminophenethyl)piperidine with 4-fluorobenzoyl chloride according to the procudure of Example 114 affords 4-fluoro-2'-[2-(1-methyl-2-piperidyl)ethyl]benzanilide, m.p. 115.5°-116.5° C. (corr.), from isopropyl ether.

Analysis. Calcd. for $C_{21}H_{25}FN_2O$: C, 74.10; H, 7.41; N, 8.23. Found: C, 74.18; H, 7.35; N, 8.26.

EXAMPLE 122

2'-[2-(1-Methyl-2-piperidyl)ethyl]-4-(trifluoromethyl)benzanilide

Reaction of 2-(o-aminophenethyl)piperidine with 4-(trifluoromethyl)benzoyl chloride according to the procedure of Example 114 affords 2'-[2-(1-methyl-2-piperidyl)ethyl]-4-(trifluoromethyl)benzanilide, m.p. 149.5°-150.0° C. (corr.), from isopropyl ether.

Analysis. Calcd. for $C_{22}H_{25}F_3N_2O$: C, 67.88; H, 6.46; N, 7.18. Found: C, 67.68; H, 6.39; N, 7.12.

EXAMPLE 123

4-(t-Butyl)-2'-[2-(1-methyl-2-piperidyl)ethyl]-benzanilide hemimucate hemiethanolate Reaction of 2-(o-aminophenethyl)piperidine with 4-(t-butyl)benzoyl chloride according to the procedure of Example 114 affords 4-(t-butyl)-2'-[2-(1-methyl-2-piperidyl)ethyl]benzanilide hemimucate hemiethanolate, m.p. 101°-120.5° C. (corr.) bubbles, from absolute ethanol.

Analysis. Calcd. for $C_{25}H_{34}N_{20}O.\frac{1}{2}C_6H_{1\text{-}0}O_{8.}\frac{1}{2}C_2H_5OH$: C, 68.75; H, 8.36; N, 5.53. Found: C, 68.43; H, 8.32; N, 5.41.

EXAMPLE 124

4-Dimethylamino-2'-[2-(1-methyl-2-piperidyl)ethyl]-benzanilide

Reaction of ethyl 4-dimethylaminobenzolate with 2-(o-aminophenethyl)-1-methylpiperidine according to the procedure of Example 115 provides 4-dimethylamino-2'-[2-(1-methyl-2-piperidyl)ethyl]benzanilide, m.p. 115°-116.5° C. (corr.), from isopropyl etherethyl acetate.

Analysis. Calcd. for $C_{23}H_{31}N_3O$: C, 75.58; H, 8.55; N, 11.50. Found: C, 75.94; H, 8.63; N, 11.52.

EXAMPLE 125

2'-[2-(1-Methyl-2-piperidyl)ethyl]-3-furancarboxanilide

Reaction of ethyl furan-3-carboxylate prepared by the method of Boyd et al, Synthesis, 545, (Oct. 1971) with 2-(2-aminophenethyl)-1-methylpiperidine according to the procedure of Example 115 provides 2'-[2-(1-methyl-2-piperidyl)ethyl]-3-furancarboxanilide, m.p. 114.5°-115.5° C. (corr.), from isopropyl ether and then ethyl acetate.

Analysis. Calcd. for $C_{19}H_{24}N_2O_2$: C, 73.04; H, 7.74; N, 8.97. Found: C, 73.30; H, 7.58; N, 9.02.

EXAMPLE 126

2'-[2-(1-Methyl-2-piperidyl)ethyl]isonicotinanilide hydrate

Reaction of 2-(o-aminophenethyl)piperidine with ethyl isonicotinate according to the procedure of Example 115 affords 2'-[2-(1-methyl-2-piperidyl)ethyl-]isonicotinanilide hydrate, m.p. 93°-100.5° C. (corr.), from ethyl acetate saturated with water.

Analysis, Calcd. for $C_{20}H_{25}N_3OH_2O$: C, 70.35; H, 7.97; N, 12.31. Found: C, 70.64; H, 7.82; N, 12.25.

EXAMPLE 127

2'-[2-(1-Methyl-2-piperidyl)ethyl]nicotinanilide

Reaction of 2-(o-aminophenethyl)piperidine with ethyl nicotinate according to the procedure of Example 115 affords 2'-[2-(1-methyl-2-piperidyl)ethyl]nicotinanilide, m.p. 88°-90° C. (corr.), from isopropyl ether.

Analysis. Calcd. for $C_{20}H_{25}N_3O$: C, 74.27; H, 7.79; N, 12.99. Found: C, 74.32; H, 7.76; N, 12.97.

EXAMPLE 128

2'-[2-(1-Ethyl-2-piperidyl)ethyl]cinnamanilide

Reaction of 2-(2-aminophenethyl)-1-ethylpiperidine with cinnamoyl chloride according to the procedure of Example 25 provides 2'-[2-(1-ethyl-2-piperidyl)]cinnamanilide, m.p. 119.5°-121.5° C. (corr.), from ethyl acetate and then acetonitrile.

Analysis. Calcd. for $C_{24}H_{30}N_2O$: C, 79.51; H, 8.34; N, 7.73. Found: C, 79.49; H, 8.44; N, 7.57.

EXAMPLE 129

2'-[2-(1-Methyl-2-piperidyl)ethyl]phenylpropiolanilide.

Reaction of ethyl propiolate with 2-(o-aminophenethyl)-1-methylpiperidine according to the procedure of Example 115 affords 2'-[2-(1-methyl-2-piperidyl(ethyl]-phenylpropiolanilide, m.p. 104.5°-106.5° C. (corr.), from ethyl acetate.

Analysis, Calcd. for $C_{23}H_{26}N_2O$: C, 79.73; H, 7.56; N, 8.09. Found: C, 79.62; H, 7.63; N, 8.15.

EXAMPLE 130

2'-[3-(1-Methyl-2-piperidyl)propyl]cinnamanilide

A solution of 4-methoxy-2'-[3-(1-methyl-2-piperidyl)-propyl]benzanilide (3.5 g., 0.0095 mole) and concentrated HCl (50 ml.) is heated at reflux for 16 hr., diluted with $H_2O$ (100 ml.), basified with 50% NaOH, and extracted with $Et_2O$. The $Et_2O$ extracts are combined, washed ($H_2O$ and saturated NaCl), dried over $MgSO_4$, and concentrated to give 2.2 g. of 2-(o-aminophenylpropyl)-1-methylpiperidine. The amine is dissolved in pyridine (50 ml.) and a solution of cinnamoyl chloride (1.8 g., 0.011 mole) in THF (10 ml.) added. The reaction mixture is stirred for 3 hr., then concentrated to dryness. The residue is dissolved in water, basified with 50% NaOH, and extracted with EtOAc. The EtOAc extracts are washed ($H_2O$+saturated NaCl), dried over magnesium sulfate, and concentrated to give 3.4 g. of oil which is chromatographed on silica AR CC-7 (Mallinckrodt). Elution first with $CHCl_3$ to remove impurities, then with EtOAc to remove the product and concentration of the EtOAc eluate gave 2.3 g. of solid which crystallized from EtOAc yields 1.6 g (46%) of 2'-[3-(1-methyl-2-piperidyl)propyl]cinnamanilide, m.p. 130°-132° C. Further crystallization from ethyl acetateisopropyl ether provides analytically pure product, m.p. 133.5°-134.5° C.

Analysis. Calcd. for $C_{24}H_{30}N_2O$: C, 79.51; H, 8.34; N, 7.73. Found: C, 79.81; H, 8.50; N, 7.55.

EXAMPLE 131

4-Methoxy-4',5'-methylenedioxy-2'-[2-(1-methyl-2-piperidyl)ethyl]benzanilide a 2-(4,5-Methylenedioxy-2-nitrostyryl)pyridine A mixture of 6-nitropiperonal (95 g., 0.487 mole), 2-picoline (45.3 g., 0.487 mole) and acetic anhydride (99.5 g., 0.974 mole) is heated under reflux for 24 hr. The resulting solution is poured into water and the precipitate which forms is collected. Crystallization from EtOAc affords 65.9 g. (51%) of 2-(4,5-methylenedioxy-2-nitrostyryl)pyridine, m.p. 167°-170° C.

Analysis. Calcd. for $C_{14}H_{10}N_2O_4$: C, 62.22; H, 3.73; N, 10.37. Found: C, 62.34; H, 3.46; N, 10.17.

b. 4-Methoxy-4',5'-methylenedioxy-2'[2-(2-pyridyl)ethyl]-benzanilide 2-(4,5-Methylenedioxy-2-nitrostyryl)pyridine (10.8 g., 0.04 mole) is hydrogenated on a Parr apparatus in 200 ml. of ethanol with 2.0 g. of 10% palladium on carbon as catalyst. After the reduction is complete, the mixture is filtered and the solvent evaporated. The residue consisting of 2-(4,5-methylenedioxy-2-aminophenethyl)pyridine is immediately dissolved in pyridine (100 ml.) and anisoyl chloride (7.5 g., 0.044 mole) added. The solution is stirred for 30 min. A basic workup according to the procedure of Example 25 affords 10 g. of 4-methoxy-4',5'-methylenedioxy-2'-[2-(2-pyridyl)ethyl]-benzanilide obtained analytically pure by crystallization from ethyl acetate.

Analysis. Calcd. for $C_{22}H_{20}N_2O_4$: C, 70.20; H, 5.36; N, 7.44. Found: C, 70.20; H, 5.45; N, 7.40.

c. 4-Methoxy-4',5'-methylenedioxy-2'-[2-(1-methyl-2-pyridinium)-ethyl]benzanilide methylsulfate.

To a solution of 4-methoxy-4',5'-methylenedioxy-2'-[2-(2-pyridyl)ethyl]benzanilide in acetone (200 ml.) is added dimethyl sulfate (3.32 g., 0.0264 mole). After 18 hr. at reflux, the mixture is cooled, 4-methoxy-4',5'-methylenedioxy-2'-[2-(1-methyl-2-pyridinium)ethyl]-benzanilide methylsulfate collected and used in the following step without further purification.

d. 4-Methoxy-4',5'-methylenedioxy-2'-[2-(1-methyl-2-piperidyl)-ethyl]benzanilide.

Reduction of 4-methoxy-4',5'-methylenedioxy-2'-[2-(1-methyl-2-pyridinium)ethyl]benzanilide methyl sulfate (9.6 g., 0.024 mole) in a Parr apparatus in 100 ml. of ethanol using $PtO_2$(0.2 g.) as catalyst according to the procedure of Example 1 yields 4-methoxy-4',5'-methylenedioxy-2'-[2-(1-methyl-2-piperidyl)ethyl]benzanilide, m.p. 112°-113° C. (corr.), from methanol-water and then ethyl acetate-isopropyl ether.

Analysis. Calcd. for $C_{23}H_{28}N_2O_4$: C, 69.67; H, 7.12; N, 7.07. Found,: C, 69.66; H, 7.33; N, 6.85.

Example 132

2'-[(1-Methyl-2-piperidyl)methyl]-p-anisanilide a. 4-Methoxy-2'-[hydroxy(2-pyridyl)methyl]benzanilide.

Pyridyl lithium, prepared by adding 2-bromopyridine (30.0 g., 0.19 mole) in 200 ml. of ether to 131 ml. of a hexane solution of 1.6 mole n-butyl lithium (0.2 mole) at −70° C., is added in 25 min. to a solution of o-(4-methoxybenzamido)benzaldehyde (8.9 g., 0.035 mole) in 300 ml. of tetrahydrofuran at −25° C. over a 20 min. period with stirring. Stirring is continued for 20 min. at −25° C. 1 hr. at −10° C. and then at 0° C. for 30 min. The reaction mixture is poured into 1500 ml. of cold 1 N hydrochloric acid, the aqueous layer separated, washed with ethyl acetate, made strongly basic with concentrated ammonium hydroxide and extracted with ethyl acetate. The ethyl acetate extract is washed with water, brine, dried over sodium sulfate and concentrated and the residue thus obtained triturated with ether to provide a 46% yield of 4-methoxy-2'-[hydroxy(2-pyridyl)-methyl]benzanilide, m.p. 127.5°-128.5° C. (corr.).

b. 2'-(2-Pyridylmethyl)-p-anisanilide.

Treatment of 4-methoxy-2'-[hydroxy(2-pyridyl)methyl]benzanilide with hydrogen iodide according to the procedure of Miller, et al., J. Org. Chem., 24, 1364 (1959) provides 2'-(2-pyridylmethyl)-p-anisanilide, m.p. 130.5°-131.5° C. (corr.), from methanol.

c. 2-[2-(p-Methoxybenzamido)benzyl]pyridinium iodide.

2'-(2-Pyridylmethyl)-p-anisanilide (9.5 g., 0.03 mole) and 0.3 mole of methyl iodide in 100 ml. of acetone is refluxed with stirring for a period of 64 hr. The reaction mixture filtered and the filter cake washed with acetone provides a 93% yield of 2-[2-(p-methoxybenzamido)-benzyl]-1-methylpyridinium iodide, m.p. 184°-186° C. (corr.).

d. 2'-[(1-Methyl-2-piperidyl)methyl]-p-anisanilide.

An ethanol (150 ml.) solution of 2-[2-(p-methoxybenzamido)benzyl]pyridinium iodide (9.2 g., 0.02 mole) hydrogenated in a Parr apparatus employing 0.2 g. of platinum oxide provides 2'-[(1-methyl-2-piperidyl)methyl]-p-anisanilide, m.p. 156°-157° C. (corr.), from water-methanol.

Analysis. Calcd. for $C_{21}H_{26}N_2O_2$: C, 74.52; H, 7.74; N, 8.28. Found: C, 74.36; H, 7.66; N, 8.29.

EXAMPLE 133

2'-[1-(1-Methyl-2-piperidyl)ethyl]-p-anisanilide a. 2'-(2-Pyridinecarbonyl)-p-anisanilide Oxidation of 2'-[hydroxy(2-pyridyl)methyl]-p-anisanilide with chromic anhydridepyridine according to the procedure of Ratcliffe, et al., J. Org. Chem., 35, 4000 (1970) provides 2'-(2-pyridinecarbonyl)-p-anisanilide, m.p. 132°-133° C. (corr.), from aqueous isopropanol.

b. 2'-[1-(2-Pyridyl)ethylidene]-p-anisanilide.

Methyl lithium (0.24 mole, 142 ml. of 1.7 molar in ether) is added to 2'-(2-pyridinecarbonyl)-p-anisanilide (36.6 g., 0.11 mole) in 400 ml. of tetrahydrofuran in 15 min. with stirring at 10°-20° C. Stirring is continued for another 30 min., the reaction mixture hydrolyzed by addition of 300 ml. of water, concentrated under reduced pressure until the tetrahydrofuran solvent is substantially removed, and the mixture extracted with ethyl acetate. The ethyl acetate extract washed with water, brine, dried over sodium sulfate and concentrated affords a residual dark brown oil. The residue taken up in benzene and diluted with hexane affords 2'-[1-hydroxy-(2-pyridyl)ethyl]-p-anisanilide, m.p. 127°-128° C., from aqueous-methanol.

2'-[1-Hydroxy-1-(2-pyridyl)ethyl]-p-anisanilide can alternatively be prepared by reaction of pyridyl lithium with o-(4-methoxybenzamido)acetophenone according to the procedure of Example 132 (a).

2'-[1-Hydroxy-1-(2-pyridyl)ethyl]-p-anisanilide (12.0 g., 0.0344 mole) is dehydrated by heating in 150 ml. of 6 N hydrochloric acid at steam bath temperature for 4 hr. The reaction mixture is poured into ice water and made basic with concentrated ammonium hydroxide. Extraction of the basified mixture with ethyl acetate, washing the ethyl acetate extract with water, brine, and drying over sodium sulfate provides on concentration 9.9 g. of residual brown oil which is further purified by dissolving in benzene and passing through a column of alumina yielding 6.0 g. of 2'-[1-(2-pyridyl)ethylidene]-p-anisanilide.

c. 2'-1-(2-Pyridyl)ethyl-p-anisanilide

2'-[1-(2-Pyridyl)-ethylidene]-p-anisanilide (6.0 g., 0.018 mole) is reduced in a Parr apparatus in 100 ml. of acetic acid employing 1.0 g. of 10% palladium on carbon catalyst. The catalyst is collected, the filtrate concentrated under reduced pressure and the residue thus obtained distributed between water and ethyl acetate. This mixture is made basic with concentrated ammonium hydroxide and the ethyl acetate extract separated, dried, and concentrated to provide 2'-1-(2-pyridyl)ethyl-p-anisanilide, m.p. 125°-126° C. (corr.), from aqueous ethanol.

d. 2'-[1-(1-Methyl-2-piperidyl)ethyl]-p-anisanilide.

2'-[1-(2-Pyridyl)ethyl]-p-anisanilide alkylated with dimethylsulfate in methanol solution provides 2-]2-(p-methoxybenzamido)-α-methylbenzyl]1-methylpyridinium iodide. Reduction of the pyridinium iodide according to the procedure of Example 132 (d) provides the diastereoisomers of 2'-[1-(1-methyl-2-piperidyl)ethyl]-p-anisanilide. The diastereoisomers are separated into racemic modifications by chromatogaphy employing a column of silica gel with ethyl acetate as solvent. Racemate A has a melting point of 151.5°-152° C. (corr.), from aqueous methanol, nmr ($CDCl_3$)δ2.00 (s, N—$CH_3$) and Racemate B has a melting point of 175.5°-179° C. (corr.), from benzene-isopropyl ether, nmr ($CDCl_3$)δ2.10 (s, N—$CH_3$).

Analysis. Calcd. for $C_{22}H_{28}N_2O_2$: C, 74.96; H, 8.01; N, 7.95. Found: Racemate A; C, 75.22; H, 8.02; N, 7.68. Racemate B; C, 75.22; H, 7.82; N, 7.91.

EXAMPLE 134

2'-[1-(1-Methyl-2-piperidyl)-2-propyl]-p-anisanilide a. 2-(p-Bromophenyl)-1-(2-pyridyl)propene 2-(p-Bromophenyl)-1-(2-pyridyl)-2-propanol is prepared from p-bromoacetophenone and 2-picoline according to the method of Villani, et al., J. Med. Chem., 13, 359 (1970) in 63% yield. This alcohol (129.1 g.) is dehydrated by heating in 1150 ml. of acetic acid-12 N hydrochloric acid (3:1) at reflux temperature for 4 hr. The mixture is evaporated in vacuo, made basic with concentrated ammonium hydroxide, and extracted with ethyl acetate. The ethyl acetate extract is washed with water and brine, dried over sodium sulfate, and evaporated to give a dark brown oil. A solution of the oil in benzene is passed through a column of silica gel. Evaporation of the eluate gave 46.4 g (26% yield) of crystalline 2-(p-bromophenyl)-1-(2-pyridyl)propene, m.p. 71.5°-73.5° C. (corr.).

Analysis. Calcd. for $C_{14}H_{12}NBr$: C, 61.32; H, 4.41; N, 5.11. Found: C, 61.04; H, 4,46; N, 4.85.

b. 2-(p-Bromophenyl)-1-(2-pyridyl)propene

A solution of 2-(p-bromophenyl)-1-(2-pyridyl)propene (16.6 g., 0.06 mole) in 200 ml. of absolute ethanol containing 0.6 g. of $PtO_2$ is shaken in a Parr apparatus until one molecular equivalent of hydrogen is taken up. The catalyst is removed by filtration, and the filtrate is evaporated to a semisolid residue which is triturated with hexane. The hexane soluble portion of this residue is chromatographed on alumina using benzene to obtain 13.1 g. (81%) of oily 2-(p-bromophenyl)-1-(2-pyridyl)propene. Distillation affords analytically pure 2-(p-bromophenyl)-1-(2-pyridyl)propene, b.p. 100°-113° C. (0.2 mm. Hg.), $n_D^{28}$ 1.5786-1.5820.

Analysis. Calcd. for $C_{14}H_{14}BrN$: C, 60.88; H, 5.11; N, 5.08. Found: C, 60.89; H, 5.05; N, 4.88.

c. 2-(4-Bromo-2-nitrophenyl)-1-(2-pyridyl)propane 2-(p-Bromophenyl)-1-(2-pyridyl)propane (11.5 g., 0.043 mole) is heated in 80 ml. of concentrated nitic acid (specific gravity 1.42, 69-71%) for 4.5 hr. at 80° C. The solution is cooled, quenched in 300 g. of ice, made alkaline with sodium hydroxide, and extracted with ethyl acetate. The extract washed with water and brine, dried over sodium sulfate, and evaporated affords 12.2 g. (88%) of oil nitrated product of sufficient purity to be used in following "step (d)". Distillation provides analytically pure 2-(4-bromo-2-nitrophenyl)-1-(2-pyridyl)propane, b.p. 172°-176° C. (0.2 mm. Hg.), $n_D^{29}$ 1.5968.

Analysis. Calcd. for $C_{14}H_{13}N_2O_2Br$: C, 52.35; H, 4.08; N, 8.73. Found: C, 52.72; H, 4.16; N, 8.44.

d. 2-(o-Anisamido)-1-(2-pyridyl)propane 2-(4-Bromo-2-nitrophenyl)-1-(2-pyridyl)propane (27.5 g., 0.086 mole) in 200 ml. of absolute ethanol containing 9.5 g. of triethylamine and 3.5 g. of 10% palladium on carbon is reduced under 3 atmospheres of hydrogen. The reduced mixture is filtered and the filtrate concentrated affords an oily residue which is taken up in 200 ml. of pyridine. Anisoyl chloride (16.1 g., 0.094 mole) is added to the pyridine solution of 2-(2-aminophenyl)-1-(2-pyridyl)propane at 10°-20° C. in 3 minutes. The mixture is stirred overnight at room temperature and evaporated in vacuo. The residue is distributed between water and ethyl acetate and made basic with concentrated ammonium hydroxide. The ethyl acetate layer is separated, washed with water, brine and evaporated to provide 30.4 g. of 2-(o-anisamido)-1-(2-pyridyl)propane. Analytically pure 2-(o-anisamido)-1-(2-pyridyl)propane is obtained by chromatography employing silica gel and using chloroform as solvent.

Analysis. Calcd. for $C_{22}H_{22}N_2O_2$: C, 76.27; H, 6.40; N, 8.09. Found: C, 75.94; H, 6.45; N, 7.86.

e. 2'-[1-(1-Methyl-2-piperidyl)-2-propyl]-p-anisanilide

A mixture of 2-(o-anisamido)-1-(2-pyridyl)propane (11.0 g., 0.32 mole) and dimethylsulfate (6.0 g., 0.048 mole) is heated at reflux overnight in 200 ml. of methyl alcohol to provide a pyridinium salt. After platinum oxide is added to the methanolic (0.4 g.) solution, the mixture is reduced under 3 atmospheres until reduction of the pyridinium salt is complete. The catalyst is removed by filtration and the filtrate evaporated to afford 2'-[(1-methyl-2-piperidyl)-2-propyl]-p-anisanilide as an oily mixture of diastereoisomers. Partial purification is carried out by chromatography using silica gel and employing ethyl acetate as the solvent. A solution of the resultant oil in benzene, diluted with isopropyl ether, provides a white, crystalline solid. Crystallization of the white solid from isopropyl acetate-isopropyl ether yields a racemic modification of 2'-[1-(1-methyl-2-piperidyl)-2-propyl]-p-anisanilide having a melting point of 124°-125° C. (corr.), nmr ($CDCl_3$), δ 2.19 (s, N—$CH_3$).

Analysis. Calcd. for $C_{23}H_{30}N_2O_2$: C, 75.37; H, 8.25; N, 7.64. Found: C, 75.42; H, 8.37; N, 7.61.

Evaporation of the mother liquors gives a heavy oil containing, according to nmr, both diastereoisomers of 2'-[1-(1-methyl-2-piperidyl)-2-propyl]-p-anisanilide in an approximate ratio of 30:70, ($CDCl_3$), δ 2.19 (s, N—$CH_3$) and δ 2.23 (s, N—$CH_3$).

Analysis. Found: C, 75.23; H, 8.18; N, 7.44.

EXAMPLE 135

2'-[1-Hydroxy-3-(1-methyl-2-piperidyl)propyl]-p-anisanilide

A mixture of o-nitrobenzaldehyde (45.3 g., 0.30 mole) triethyl orthoformate (48.8 g., 0.33 mole), 75 ml. absolute ethanol, and 10 drops ethanolic HCl is stirred overnight. Potassium carbonate (6.0 g.) is added to the solution to neutralize the acid, and the reaction mixture filtered. The filtrate, with 2.0 g. of 10% Pd/C, is shaken on a Parr apparatus, rapidly reducing the nitro group. The catalyst is collected, and $Et_3N$ (126 ml.) added to the filtrate. The solution is cooled as anisoyl chloride (63.9 g., 0.38 mole) in benzene is added dropwise. After standing overnight, the reaction mixture is concentrated to dryness to remove excess $Et_3N$ and the residue is dissolved in 950 ml. of EtOH and 250 ml. of 1 N HCl added. The solution is cooled, providing a precipitate which is collected yielding 63.8 g. (83%) of solid, m.p. 99.5°-100.5° C. Analytically pure o-(4-methoxybenzamido)benzaldehyde has a melting point of 99.5°-100.5° C., from ethanol.

Analysis. Calcd. for $C_{15}H_{13}NO_3$: C, 70.58; H, 5.13; N, 5.49. Found: C, 70.28; H, 4.98; N, 5.61.

2-(N-Methyl-2-piperidyl)ethylmagnesium chloride is prepared in 200 ml. of tetrahydrofuran from Mg shavings (5.6 g., 0.230 g.-atom) and 2-(2-chloroethyl)-1-methylpiperdine (33.4 g., 0.206 mole). The mixture is heated at reflux during the addition of the chloride and for a 22 hr. period after the addition. After cooling to room temperature, a solution of o-(4-methoxybenzamido)benzaldehyde (17.5 g., 0.069 mole) in 235 ml. tetrahydrofuran is added dropwise. The mixture is heated at reflux for 3 hr., cooled and hydrolyzed with 27 ml. of saturated aqueous $NH_4Cl$. The solution is filtered and evaporated to give a residue which is dissolved in 125 ml. of $CH_3CN$. The first crop obtained on cooling is collected, 12.8 g., m.p. 131°-136° C., and recrystallized five times from $CH_3CN$, yielding 4.1 g. of 2'-[1-hydroxy-3-(1-methyl-2-piperidyl)propyl]-p-anisanilide (Racemate B), m.p. 148.0°-149.0° C. (corr.).

Further cooling of the mother liquor from the first crop affords 6.1 g. of additional product, m.p. 119°-125° C. Crystallization from $CH_3CH$ yields 1.8 g. of 4-methoxy-2'-[1-hydroxy-3-(1-methyl-2-piperidyl)-propyl]benzanilide (Racemate A), m.p. 129.5°-130.5° C. (corr.).

Analysis. Calcd. for $C_{23}H_{30}N_2O_3$: C, 72.22; H, 7.91; N, 7.32. Found: (Racemate A); C, 72.39; H, 7.92; N, 7.25; (Racemate B); C, 72.10; H, 7.69; N, 7.36.

EXAMPLE 136

4-Methoxy-2'-[3-(1-methyl-2-piperidyl)propyl]-benzanilide

A mixture of 5% Pd/$BaSO_4$ and AcOH (100 ml.) is shaken on a Parr hydrogenator for 0.5 hr. prior to adding a solution of 4-methoxy-2'-[1-hydroxy-3-(1-methyl-2-piperidyl)propyl]benzanilide (8.0 g., 0.021 mole), AcOH (150 ml) and 70% $HClO_4$ (8.0 ml, 0.09 mole). The hydrogenation is complete in about 3 hr. The catalyst is filtered off and 50% NaOH (5 ml.) added to the filtrate to neutralize the $HClO_4$. After concentration, dilution with $H_2O$ and basification with 50% NaOH, the mixture is extracted with EtOAc. The EtOAc extract is washed with water, dried over magnesium sulfate and concentrated to give an oil, 8.3 g., which is crystallized from 75 ml. of EtOAc. The product, m.p. 107°-110° C., is filtered off and recrystallized from EtOAc, providing 4.2 g. (55%) of 4-methoxy-2'-[3-(1-methyl-2-piperidyl)propyl]benzanilide, m.p. 108.5°-110° C.

Analysis. Calcd. for $C_{23}H_{30}N_2O_2$: C, 75.37; H, 8.25; N, 7.64. Found: C, 75.58; H, 8.24; N, 7.55.

EXAMPLE 137

2'-(2-Piperidylmethyl)-p-anisanilide

Reduction of 2'-(2-pyridylmethyl)-p-anisanilide (4.65 g., 0.0146 mole) according to the procedure of Walker, J. Org. Chem., 27, 2966 (1962), in 150 ml. of acetic acid with 2.35 g. of 10% palladium on carbon catalyst affords 2'-(2-piperidylmethyl)-p-anisanilide, m.p. 108°-109° C. (corr.), from benzene-hexane.

Analysis. Calcd. for $C_{20}H_{24}N_2O_2$: C, 74.04; H, 7.46; N, 8.64. Found: C, 74.33; H, 7.27; N, 8.73.

EXAMPLE 138

2'-[Hydroxy(2-piperidyl)methyl]-p-anisanilide

Reduction of 2'-[hydroxy(2-pyridyl)methyl]-p-anisanilide, according to the procedure of Example 137 provides 2'-[hydroxy(2-piperidyl)methyl]-p-anisanilide, m.p. 157.5°-159.5° C. (corr.), from benzene.

Analysis. Calcd. for $C_{20}H_{24}N_2O_3$: C, 70.56; H, 7.11; N, 8.23. Found: C, 70.60; H, 7.12; N, 8.04.

EXAMPLE 139

2'-[2-(2-Piperidyl)ethyl]-p-anisanilide hemimucate

Hydrogenation of 2'-[2-(2-pyridyl)ethyl]-p-anisanilide according to the procedure of Example 117 affords 2'-[2-(2-piperidyl)-ethyl]-p-anisanilide hemimucate, m.p. 169°-169.5° C., from water and then isopropyl ether.

Analysis. Calcd. for $C_{21}H_{26}N_2O_2 \cdot \frac{1}{2}C_6H_{10}O_8$: C, 64.98; H, 7.05; N, 6.32. Found: C, 64.81; H, 7.22; N, 6.06.

EXAMPLE 140

2-[2-[(p-Methoxybenzyl)amino]phenethyl]-1-methylpiperidine hemimucate

A solution of 4-methoxy-2'-[2-(1-methyl-2-piperidyl-)ethyl]benzanilide (10 g., 0.028 mole) in 100 ml. of tetrahydrofuran is added to 150 ml. of 1 molar borane: THF complex. After stirring 1 hr. and heating under reflux 1 hr., 6 N, HCl (50 ml.) is added dropwise to the reaction mixture. The reaction mixture is evaporated and the residue dissolved in 200 ml. of water. Basification of the solution followed by ether extraction and evaporation of the dried ($MgSO_4$) ethereal extracts affords an oil which is distilled, b.p. 220° C., 0.05 Torr, and then converted to the mucate salt by treating with mucic acid in ethanol. Crystallization from water yields 5.0 g. (40%), of analytically pure 2-[2-[(p-methoxybenzyl)amino]-phenethyl]-1-methylpiperidine hemimucate, m.p. 164.5°-165.5° C. (dec.)(corr.).

Analysis. Calcd. for $C_{22}H_{30}N_2O \cdot \frac{1}{2}C_6H_{10}O_8$: C, 67.68; H, 7,96; N, 6.32. Found: C, 67.60; H, 7.80; N, 6.32.

EXAMPLE 141

Optically active 2'-[2-(1-methyl-2-piperidyl)-ethyl]cinnamanilide a. Resolution of 2-(o-aminophenethyl)-1-methylpiperidine.

Fractional crystallization of the d-camphoric acid salt of racemic 2-(o-aminophenethyl)-1-methylpiperidine from 95% EtOH provides a fraction with the following properties: m.p. 112°-132° C. $[\alpha]_D^{25°} = -4.0°$ (1% in 95% EtOH). This fraction is converted to the free base, distilled, and the portion boiling at 105°-106° C. (0.02 Torr), $n_D^{30°}$1.5546 collected (stereoiosomer A). A dihydrochloride of 2-(o-aminophenethyl)-1-methylpiperidine stereoisomer A has the following properties: m.p. 240°-250° C.; $[\alpha]_D^{25°} = -12.9°$ (1% in 95% EtOH).

Analysis. Calcd. for $C_{14}H_{22}N_2 \cdot 2HCl$: C, 57.73; H, 8.31; N, 9.62. Found: C, 57.77; H, 8.51; N, 9.58.

The ethanolic mother liquors, enriched in the d-camphoric acid salt of stereoisomer B from the isolation of 2-(o-aminophenethyl)-1-methylpiperidine (stereoisomer A), are evaporated and the residue converted to the free base. The base is converted to the 1-camphoric acid salt which is fractionally crystallized from 95% EtOH. Two fractions are obtained having a rotation of $[\alpha]_D^{25°} = +4.1°$ (1% in 95% EtOH) and $[\alpha]_D^{25°} = +4.4°$ (1% in 95% EtOH). These fractions combined, converted to the free base and chromatographed (alumina, EtOAc) to remove a small amount of a polar impurity, provide 2(o-aminophenyl)-1-methyl piperidine (stereoisomer B).

b. 1-2'-[2-(1Methyl-2-piperidyl)ethyl]cinnamanilide.

Reaction of 2-(o-aminophenethyl)-1-methylpiperidine (stereoisomer A) and cinnamoyl chloride according to the procedure of Example 25 affords 1-2'-[2-(1-methyl-2-piperidyl)ethyl]cinnamanilide, m.p. 129°-130° C. (corr.) from ethyl acetate: $[\alpha]_D^{27°} = -42.8°$ (2% in 95% EtOH).

Analysis. Calcd. for $C_{23}H_{28}N_2O$: C, 79.27; H, 8.10; N, 8.04. Found: C, 79.09; H, 8.14; N, 7.95.

c. d-2'-[2-(1-Methyl-2-piperidyl)ethyl]cinnamanilide.

Reaction of 2-(o-aminophenethyl)-1-methylpiperidine (stereoisomer B) and cinnamoyl chloride according to the procedure of Example 25 affords d-2'-[2-(1-methyl-2-piperidyl)ethyl]cinnamanilide, m.p. 128.5°-129.5° C. (corr.) from heptane and then isopropanol) $[\alpha]_D^{26°} = +42.9°$ (2% in 95% EtOH).

analysis. Found: C, 79.46; H, 8.12; N, 7.92.

EXAMPLE 142

Optically active 4-methoxy-2'-[2-(1-methyl-2-piperidyl)ethyl]benzanilide a. 1-4-Methoxy-2'-[2-(1-methyl-2-piperidyl)ethyl]-benzanilide.

Reaction of 2-(o-aminophenethyl)-1-methylpiperidine (stereoisomer A) and anisoyl chloride according to the procedure of Example 25 affords 1-4-methoxy-2'-[2-(1-methyl-2-piperidyl)ethyl]benzanilide, m.p. 126.5°-127.5° C. (corr.), from heptane; $[\alpha]_D^{29°} = -39.3°$ (2% in 95% EtOH).

Analysis. Calcd. for $C_{22}H_{28}N_2O_2$: C, 74.96; H, 8.01; N, 7.95. Found: C, 74.97; H, 8.07; N, 7.79.

b. d-4-Methoxy-2'-[2-(1-methyl-2-piperidyl)ethyl]-benzanilide.

Reaction of 2-(o-aminophenethyl)-1-methylpiperidine (stereoisomer B) and anisoyl chloride according to the procedure of Example 25 affords d-4-methoxy-2'-[2-(1-methyl-2-piperidyl)ethyl]benzanilide, m.p. 127°-127.5° C. (corr.), from heptane; $[\alpha]_D^{25°} = +41.5°$ (2% in 95% EtOH).

Analysis. Found: C, 75.02; H, 7.76; N, 7.83.

While several specific embodiments are disclosed in the foregoing specification, it will be appreciated that other modifications may be made without departing from the spirit and scope of the appended claims.

What is claimed is:

1. A process for eliciting an antiarrhythmic effect in a mammal in need of said effect which comprises systemic administration to said mammal of a non-toxic effective antiarrhythmic dose of from about 0.01 to 20 mg./kg. of body weight of said mammal of a compound from the group consisting of a substituted piperidine having Formula I Formula I

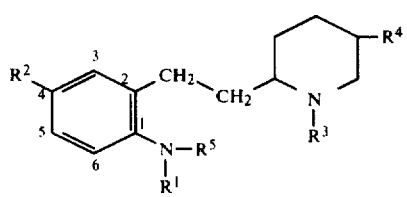

wherein $R^1$ represents hydrogen $R^2$ represents hydrogen or methylenedioxy attached in the benzenoid 4,5-position $R^3$ represents hydrogen or methyl $R^4$ represents hydrogen $R^5$ is selected from the group consisting of lower alkanoyl of from 1 to 4 carbon atoms inclusive, lower alkanesulfonyl of from 1 to 4 carbon atoms inclusive, cinnamoyl,

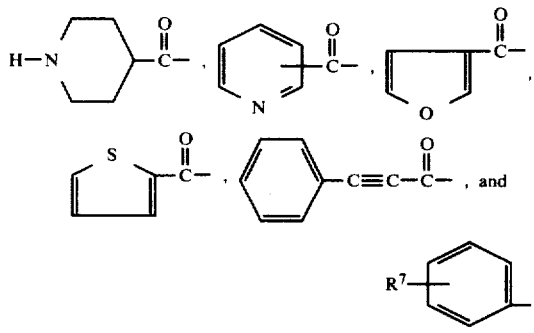

wherein $R^7$ is selected from the group consisting of hydrogen, chlorine, dimethylamino, alkylthio of from 1 to 4 carbon atoms inclusive, alkyl of from 1 to 4 carbon atoms inclusive, methoxy, 3,4-dimethoxy, 3,5-dimethoxy, and 3,4,5-trimethoxy;

and a pharmaceutically acceptable salt thereof.

2. The process of claim 1 in which the compound is 4-methoxy-2'[2-(1-methyl-2-piperidyl)ethyl]benzanilide.

3. The process of claim 1 in which the compound is 4-methoxy-2'-[2-(1-methyl-2-piperidyl)ethyl]benzanilide hydrochloride.

4. The process of claim 1 in which the compound is 4-chloro-2'-[2-(1-methyl-2-piperidyl)ethyl]benzanilide.

5. The process of claim 1 in which the compound is 2'-[2(1-methyl-2-piperidyl)ethyl]benzanilide.

6. A process for eliciting an antiarrhythmic effect in a mammal in need of said effect which comprises systemic administration to said mammal of a non-toxic effective dose of from about 0.01 to 20 mg./kg. of body weight of said mammal of a compound selected from the group consisting of a substituted piperidine having Formula XII Formula XII

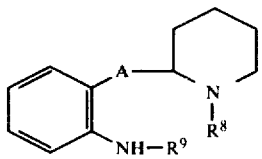

wherein $R^8$ represents lower alkyl of 1 to 4 carbon atoms inclusive;

$R^9$ is selected from the group consisting of cinnamoyl or

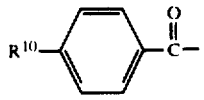

wherein

[Rd$^{10}$] $R^{10}$ is methoxy;

A is a divalent radical selected from the group consisting of $—CH_2—$,

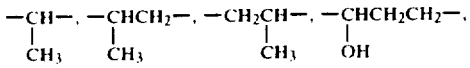

and $—(CH_2)_3—$;

and a pharmaceutically acceptable salt thereof.

7. The process of claim 6 in which the compound is 2'-[3-(1-methyl-2-piperidyl)propyl]p-anisanilide.

8. The process of claim 6 in which the compound is 2'-[(1-methyl-2-piperidyl)methyl]-p-anisanilide.

9. A process for eliciting an antiserotonin effect in a mammal in need of said effect which comprises systemic administration to said mammal of a non-toxic antiserotonin effective dose of from about 0.01 to 20 mg./kg. of body weight of said host of the compound 2'-[2-(1-methyl-2-piperidyl)ethyl]-cinnamanilide or a pharmaceutically acceptable acid addition salt thereof.

10. The process of claim 9 in which the compound is 2'-[2-(1-methyl-2-piperidyl)ethyl]cinnamanilide hydrochloride.

11. A pharmaceutical composition in dosage unit form suitable for systemic administration to a mammal comprising a pharmaceutical carrier containing from 1 to 500 milligrams of an active ingredient selected from the group consisting of a compound having Formula I Formula I

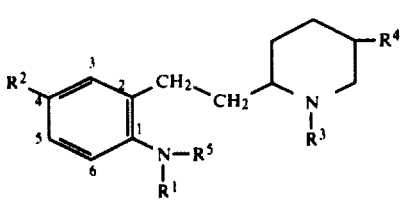

wherein $R^1$ represents hydrogen;

$R^2$ represents hydrogen or methylenedioxy attached in the benzenoid 4,5-position;

$R^3$ represents hydrogen or methyl; $R^4$ represents hydrogen;

$R^5$ is selected from the group consisting of lower alkanoyl of from 1 to 4 carbon atoms inclusive, lower alkanesulfonyl of from 1 to 4 carbon atoms inclusive, cinnamoyl,

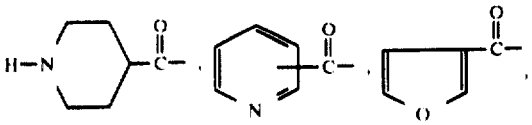

-continued

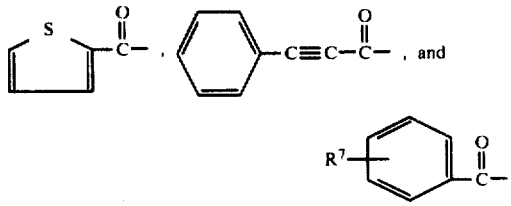

wherein $R^7$ is selected from the group consisting of hydrogen, chlorine, dimethylamino, alkylthio of from 1 to 4 carbon atoms inclusive, alkyl of from 1 to 4 carbon atoms inclusive, methoxy, 3,4-dimethoxy, 3,5-dimethoxy, and 3,4,5-trimethoxy and a pharmaceutically acceptable salt thereof.

12. The composition of claim 11 in which the active ingredient is 2'-[2-(1-methyl-2-piperidyl)ethyl]cinnamanilide.

13. The composition of claim 11 in which the active ingredient is 2'-[2-(1-methyl-2-piperidyl)ethyl]cinnamanilide hydrochloride.

14. The composition of claim 11 in which the active ingredient is 4-methoxy-2'-[2-(1-methyl-2-piperidyl)ethyl]benzanilide.

15. The composition of claim 11 in which the active ingredient is 4-methoxy-2'-[2-(1-methyl-2-piperidyl)ethyl]benzanilide hydrochloride.

16. The composition of claim 11 in which the active ingredient is 4-chloro-2'-[2-(1-methyl-2-piperidyl)ethyl]benzanilide.

17. The composition of claim 11 in which the active ingredient is 2'-[2-(1-methyl-2-piperidyl)ethyl]benzanilide.

18. A pharmaceutical composition in dosage unit form suitable for systemic administration to a mammal comprising a pharmaceutical carrier containing 1 to 500 milligrams of active ingredient selected from the group consisting of a compound having Formula XII Formula XII

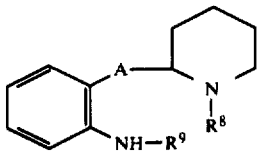

wherein $R^8$ represents lower alkyl of 1 to 4 carbon atoms inclusive;

$R^9$ is selected from the group consisting of cinnamoyl or

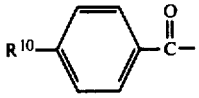

wherein $R^{10}$ is methoxy;

A is a divalent radical selected from the group consisting of $—CH_2—$, $$-\underset{\underset{CH_3}{|}}{CH}-,\ -\underset{\underset{CH_3}{|}}{CHCH_2}-,\ -CH_2\underset{\underset{CH_3}{|}}{CH}-,\ -\underset{\underset{OH}{|}}{CHCH_2CH_2}-,$$

and $-(CH_2)_3-$;

and a pharmaceutically acceptable salt thereof.

19. The composition of claim 18 in which the active ingredient is 2'-[3-(1-methyl-2-piperidyl)propyl]-p-anisanilide.

20. The composition of claim 18 in which the active ingredient is 2'-[(1 -methyl-2-piperidyl)methyl]-p-anisanilide.

*21. A process for eliciting an antiarrhythmic effect in a mammal in need of said effect which comprises systemic administering to said mammal of a non-toxic effective antiarrhythmic dose of from about 0.01 to 20 mg./kg. of body weight of said mammal of 4-hydroxy-2'-[2-(1-methyl-2-piperidyl)ethyl]benzanilide.*

*22. A pharmaceutical composition in dosage unit form suitable for systemic administration to a mammal comprising a pharmaceutical carrier containing from 1 to 500 milligrams of an active ingredient consisting of 4-hydroxy-2'-[2-(1-methyl-2-piperidyl)ethyl]benzanilide.*

* * * * *